United States Patent
Vetter et al.

(10) Patent No.: US 11,602,630 B2
(45) Date of Patent: Mar. 14, 2023

(54) SYSTEMS AND METHODS FOR FLEXIBLE ELECTRODE ARRAYS

(71) Applicant: NeuroNexus Technologies, Inc., Plano, TX (US)

(72) Inventors: Rio J. Vetter, Plano, TX (US); Peter Gerow, Plano, TX (US); David S. Pellinen, Plano, TX (US); Carlos Rackham, Plano, TX (US); Daryl R. Kipke, Plano, TX (US); Jamille F. Hetke, Plano, TX (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 528 days.

(21) Appl. No.: 16/002,992

(22) Filed: Jun. 7, 2018

(65) Prior Publication Data
US 2018/0353753 A1    Dec. 13, 2018

Related U.S. Application Data

(60) Provisional application No. 62/516,212, filed on Jun. 7, 2017.

(51) Int. Cl.
*A61B 5/05*    (2021.01)
*A61N 1/05*    (2006.01)
(Continued)

(52) U.S. Cl.
CPC ............ *A61N 1/0553* (2013.01); *A61B 5/287* (2021.01); *A61B 5/6869* (2013.01); *A61N 1/059* (2013.01);
(Continued)

(58) Field of Classification Search
CPC .................. A61B 5/318; A61B 5/0006; A61B 2560/0412; A61B 5/287; A61B 5/283;
(Continued)

(56) References Cited

U.S. PATENT DOCUMENTS 4,735,208 A    4/1988    Wyler et al.
4,903,702 A    2/1990    Putz
(Continued)

FOREIGN PATENT DOCUMENTS

CN    101876770 B    6/2013
EP    2845622    3/2015
(Continued)

OTHER PUBLICATIONS

Rousche et al., "Flexible Polyimide-Based Intracortical Electrode Arrays with Bioactive Capability," IEEE Transactions on Biomedical Engineering, vol. 48, No. 3, pp. 361-371, Mar. 3, 2001.
(Continued)

*Primary Examiner* — Joseph A Stoklosa
*Assistant Examiner* — Brian M Antiskay
(74) *Attorney, Agent, or Firm* — Haynes and Boone, LLP

(57) ABSTRACT

A medical electrode array system comprising a thin-film substrate, a plurality of electrode contacts disposed on the thin-film substrate, and a plurality of traces. The plurality of electrode contacts is configured to provide electrical contact points. The plurality of traces is electrically connected to the plurality of electrode contacts. A electrode contact of the plurality of electrode contacts has a dedicated trace of the plurality of traces that provides electrical connectivity to the electrode contact. The thin-film substrate is configured to flex to maintain continuous contact with contours of patient anatomy. The plurality of traces includes flexible spring-like portions to add flexibility to the thin-film substrate.

23 Claims, 31 Drawing Sheets

(51) Int. Cl.
  *A61B 5/00* (2006.01)
  *A61N 1/36* (2006.01)
  *A61B 5/287* (2021.01)
  *A61B 5/24* (2021.01)

(52) U.S. Cl.
  CPC ......... *A61N 1/0558* (2013.01); *A61N 1/0597* (2013.01); *A61N 1/36114* (2013.01); *A61B 5/24* (2021.01); *A61B 5/6883* (2013.01); *A61B 2562/0209* (2013.01); *A61B 2562/046* (2013.01); *A61B 2562/164* (2013.01); *A61B 2562/166* (2013.01); *A61B 2562/222* (2013.01)

(58) Field of Classification Search
  CPC   A61B 2018/00351; A61B 2018/00839; A61B 5/282; A61N 1/05; A61N 1/0558; A61N 1/37; A61N 1/362; A61N 1/0531; A61N 1/0529; A61N 1/37205; A61N 1/0553; A61N 1/0492
  USPC ................ 600/372–375, 377–378, 508–509, 600/544–545; 607/115–118
  See application file for complete search history.

(56) References Cited

U.S. PATENT DOCUMENTS

| | | | |
|---|---|---|---|
| 5,520,180 | A | 5/1996 | Uy et al. |
| 5,846,196 | A | 12/1998 | Siekmeyer et al. |
| 6,024,702 | A | 2/2000 | Iversen |
| 6,624,510 | B1 | 9/2003 | Chan et al. |
| 6,792,314 | B2 | 9/2004 | Byers et al. |
| 6,973,342 | B1 | 12/2005 | Swanson |
| 7,107,097 | B2 | 9/2006 | Stern et al. |
| 7,127,301 | B1 | 10/2006 | Okandan et al. |
| 7,326,649 | B2 | 2/2008 | Rodger et al. |
| 7,337,012 | B2 | 2/2008 | Maghribi et al. |
| 8,271,099 | B1 | 9/2012 | Swanson |
| 8,588,937 | B2 | 11/2013 | Greenberg et al. |
| 8,798,707 | B2 | 8/2014 | Choi et al. |
| 9,061,134 | B2 | 6/2015 | Askin, III et al. |
| 9,655,561 | B2 * | 5/2017 | Tilk .................... A61B 5/6805 |
| 2003/0097165 | A1 | 5/2003 | Krulevitch et al. |
| 2004/0238819 | A1 | 12/2004 | Maghribi |
| 2007/0104944 | A1 | 5/2007 | Laude et al. |
| 2007/0123963 | A1 | 5/2007 | Krulevitch |
| 2008/0058875 | A1 | 3/2008 | Greenberg et al. |
| 2010/0130844 | A1 | 5/2010 | Williams et al. |
| 2010/0204560 | A1 * | 8/2010 | Salahieh ............ A61B 18/1492 600/373 |
| 2011/0230747 | A1 | 9/2011 | Rogers et al. |
| 2013/0041235 | A1 | 2/2013 | Rogers et al. |
| 2013/0245733 | A1 | 9/2013 | Yomtov |
| 2013/0281814 | A1 * | 10/2013 | Tilt ..................... A61B 5/6805 600/382 |
| 2013/0303873 | A1 | 11/2013 | Voros et al. |
| 2014/0039290 | A1 * | 2/2014 | De Graff .......... H01L 27/14687 600/377 |
| 2016/0007874 | A1 | 1/2016 | Ma et al. |
| 2016/0067477 | A1 | 3/2016 | Dubuclet |

FOREIGN PATENT DOCUMENTS

| | | |
|---|---|---|
| WO | WO2010/056771 | 5/2010 |
| WO | WO2013131261 | 9/2013 |
| WO | WO2014176420 | 10/2014 |
| WO | WO2016/016438 | 2/2016 |
| WO | WO2016022906 | 2/2016 |

OTHER PUBLICATIONS

Cheung et al., "Flexible Polyimide Microelectrode Array for in Vivo Recordings and Current Source Density Analysis," Biosensors and Bioelectronics 22 (2007) pp. 1783-1790.

Viventi et al., "Flexible, Foldable, Actively Multiplexed, High-Density Electrode Array for Mapping Brain Activity in Vivo," Nature Neuroscience 14, pp. 1599-1605 (2011).

Patent Cooperation Treaty, European Patent Office, "Notification of Transmittal of the International Search Report and the Written Opinion of the International Searching Authority" for Application No. PCT/US2018/036555, dated Sep. 18, 2018, 13 pages.

* cited by examiner

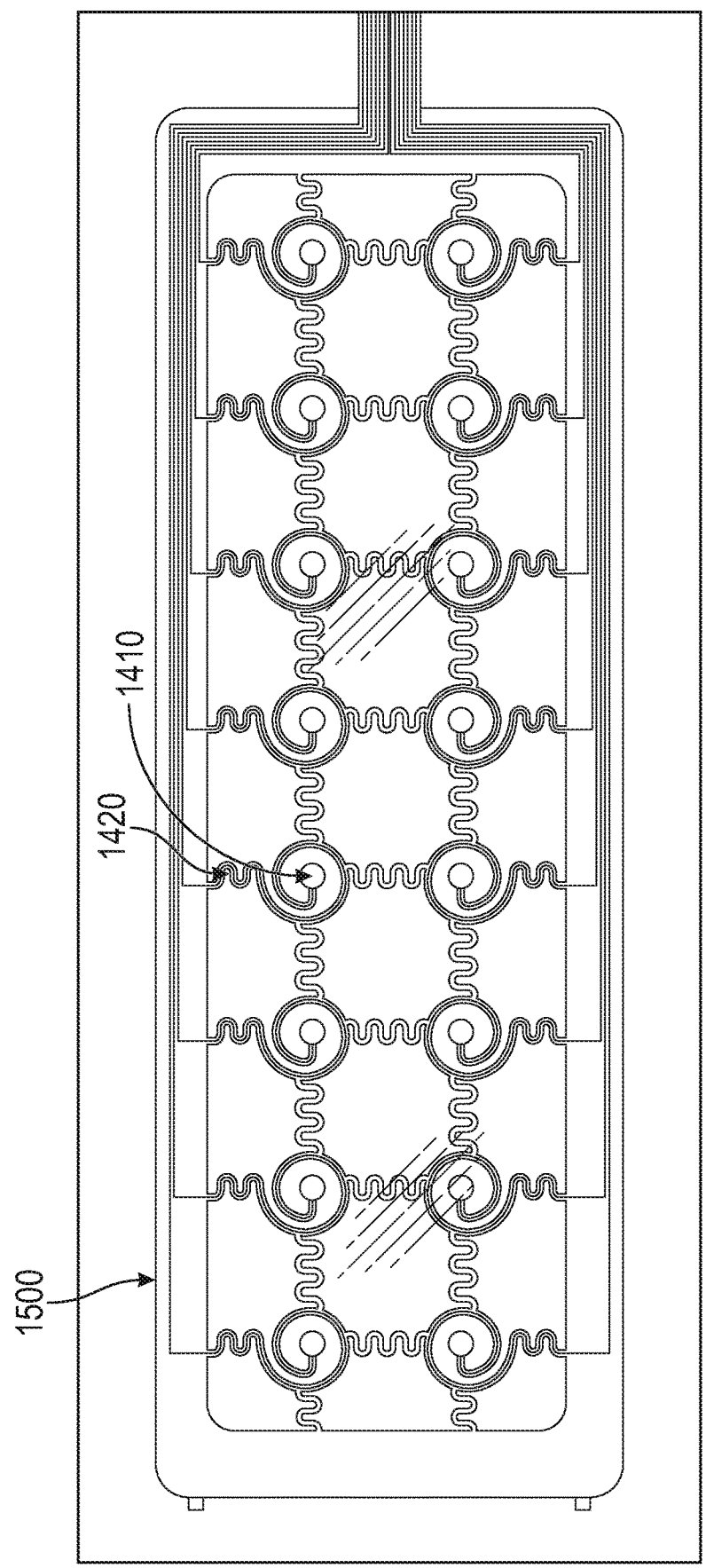

SYSTEMS AND METHODS FOR FLEXIBLE ELECTRODE ARRAYS

CROSS REFERENCE TO RELATED APPLICATION

This application claims benefit of U.S. Provisional Application No. 62/516,212, filed Jun. 7, 2017, which is incorporated herein by reference in its entirety.

FIELD

The present disclosure is directed to systems and methods for use in providing electrode arrays for medical applications, and more particularly to systems and methods for providing stretchable surface substrates for reliable electrical and mechanical contact with non-linear and moving patient anatomy.

BACKGROUND

To interface with the nervous system, electrodes may be used, including multi-contact electrode arrays. The electrode arrays may be used to transmit signals into the tissue ("stimulation") or to extract signals from the tissue ("sense"). These electrode arrays can be used in neuroscience and neurophysiological research as well as in clinical therapeutic applications. It is desirable to interface with the targeted volume in three dimensions. Commercially available electrode arrays are limited in their ability to position electrode contacts in a three-dimensional arrangement. Two examples of commercially available electrode arrays are the planar silicon array, often referred to as the "Michigan Probe," and a silicon-based technology array referred to as the "Utah Array." The Michigan Probe is limited to positioning electrode contacts in a two-dimensional arrangement, all within a single plane. The Utah Array is also limited to positioning electrode contacts in a two-dimensional plane. Moreover, electrode contacts in a Utah Array are limited to placement on the tip of each electrode shank.

However, current approaches to electrode array design may not be well adapted to penetrating tougher tissue, such as muscle. Also, conventional electrode arrays may not be well adapted to placement on non-linear contours associated with various biological tissues within the human anatomy. Conventional electrode arrays are incapable of withstanding tensile loads produced within the operating environment that cause the conventional electrode arrays to fold, buckle, twist, and/or stretch, thereby adversely affecting their functionality. These deficiencies make conventional electrode arrays undesirable for tissue stimulation or tissue sensing. To address the above shortcomings of conventional electrode arrays, the present disclosure proposes robust electrode arrays that are flexibly capable of matching non-linear contours associated with various biological tissues, and withstanding tensile loads produced within the operating environment.

SUMMARY

The embodiments of the disclosure are summarized by the claims that follow below.

In one embodiment, a medical electrode array system may include a thin-film substrate, a plurality of electrode contacts disposed on the thin-film substrate, the plurality of electrode contacts providing electrical contact points, and a plurality of traces electrically connected to the plurality of electrode contacts, each electrode contact having a dedicated trace to provide electrical connectivity to the electrode contacts. The thin-film substrate may to flex to maintain continuous contact with contours of patient anatomy. The plurality of traces may include flexible spring-like portions to add flexibility to the thin-film substrate These embodiments and others may be better understood by reference to the accompanying drawings and detailed description.

BRIEF DESCRIPTIONS OF THE DRAWINGS

Aspects of the present disclosure are best understood from the following detailed description when read with the accompanying Figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 5:
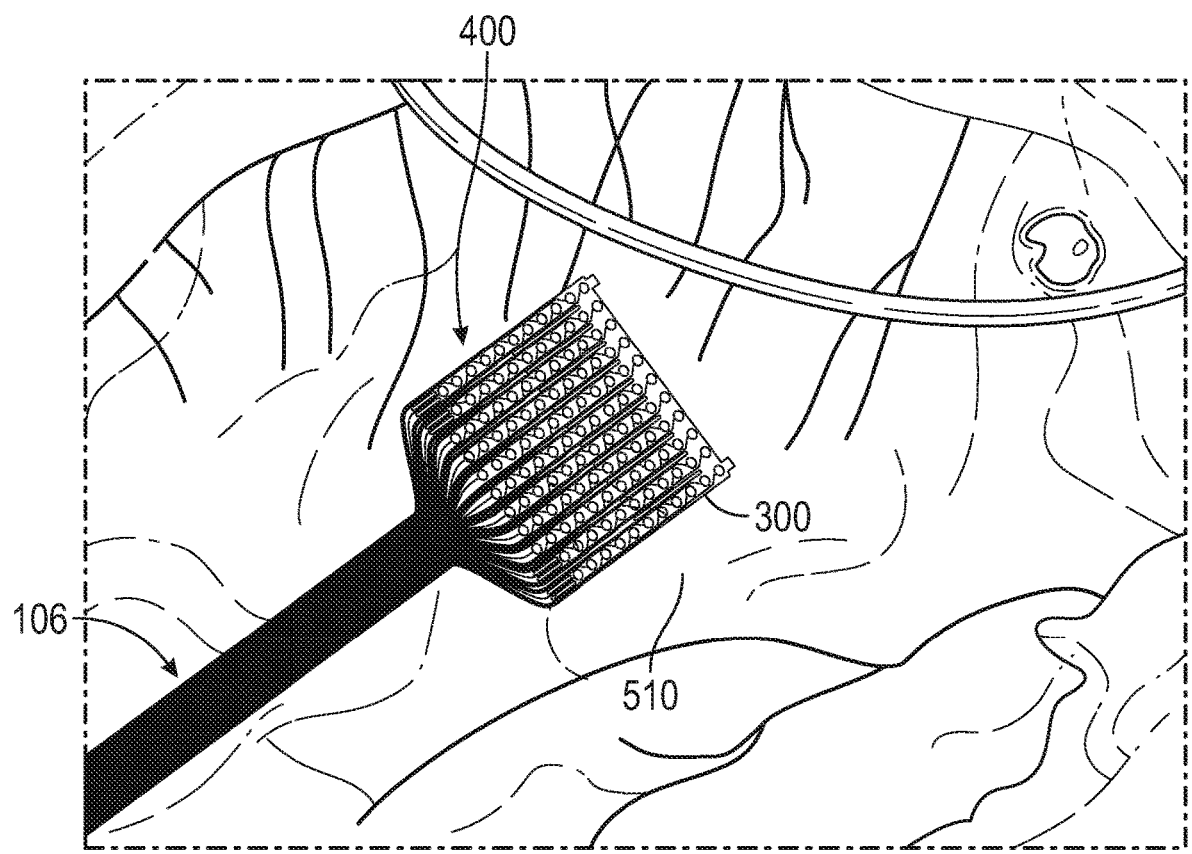

FIG. 5 shows the exemplary configuration 400 of the electrode array assembly 108 in contact with exterior biological tissue 510 of a patient's heart, according to an embodiment of the present disclosure.

Figure 6:
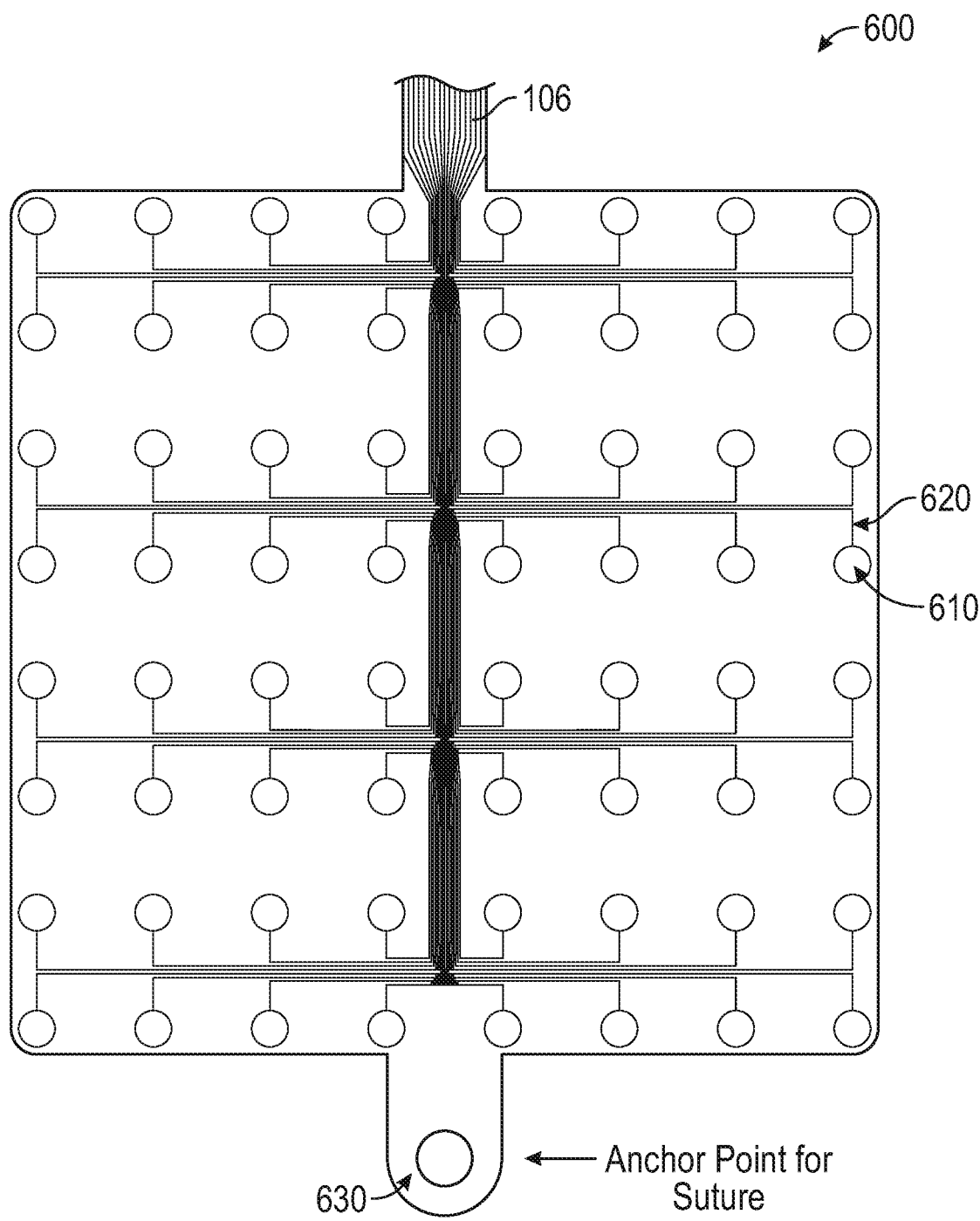

FIG. 6 shows another exemplary configuration 600 of the electrode array assembly 108 according to an embodiment of the present disclosure.

Figure 7:
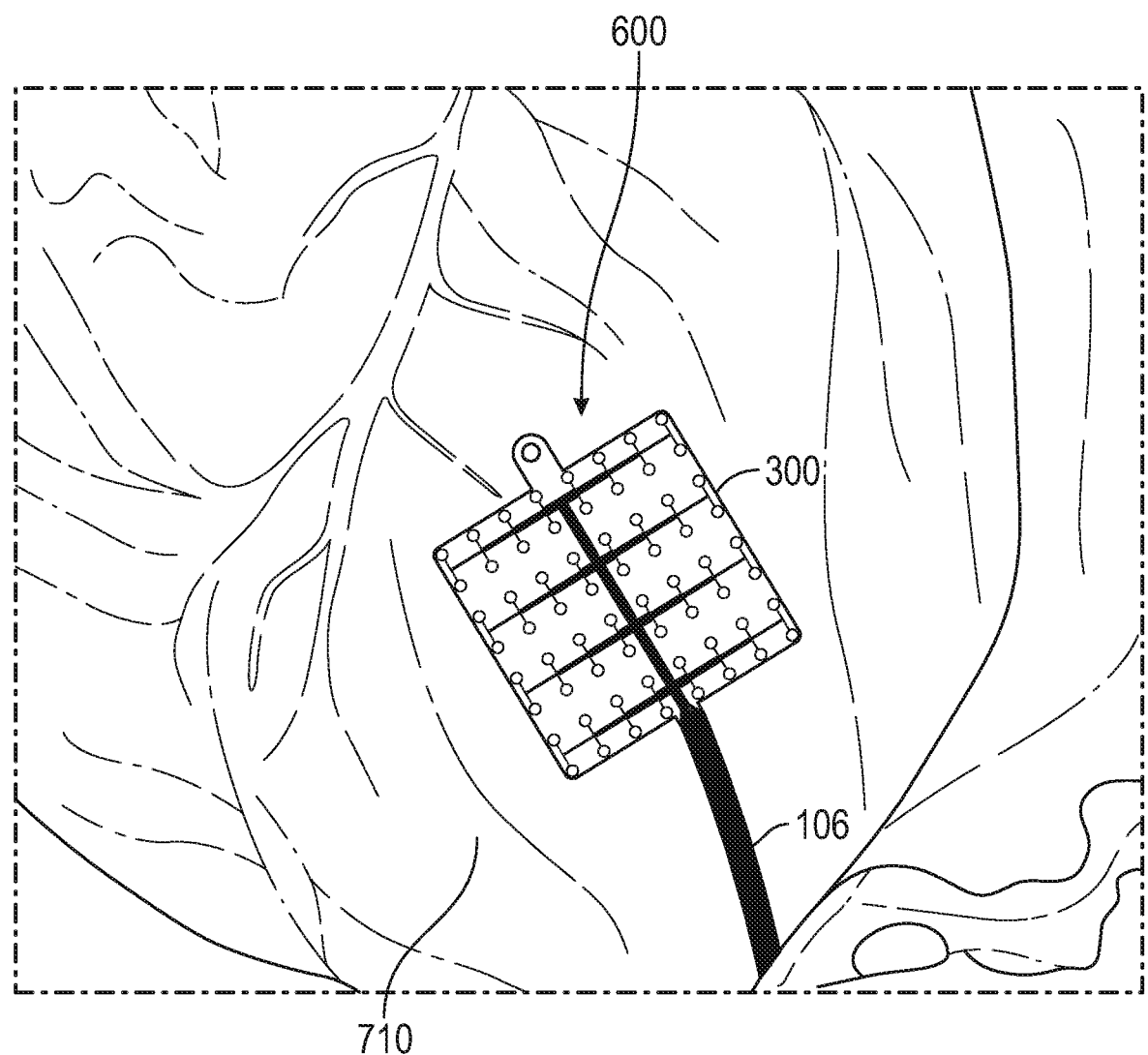

FIG. 7 shows the exemplary configuration 600 of the electrode array assembly 108 in contact with exterior biological tissue 710 of a patient's heart, according to an embodiment of the present disclosure.

Figure 8:
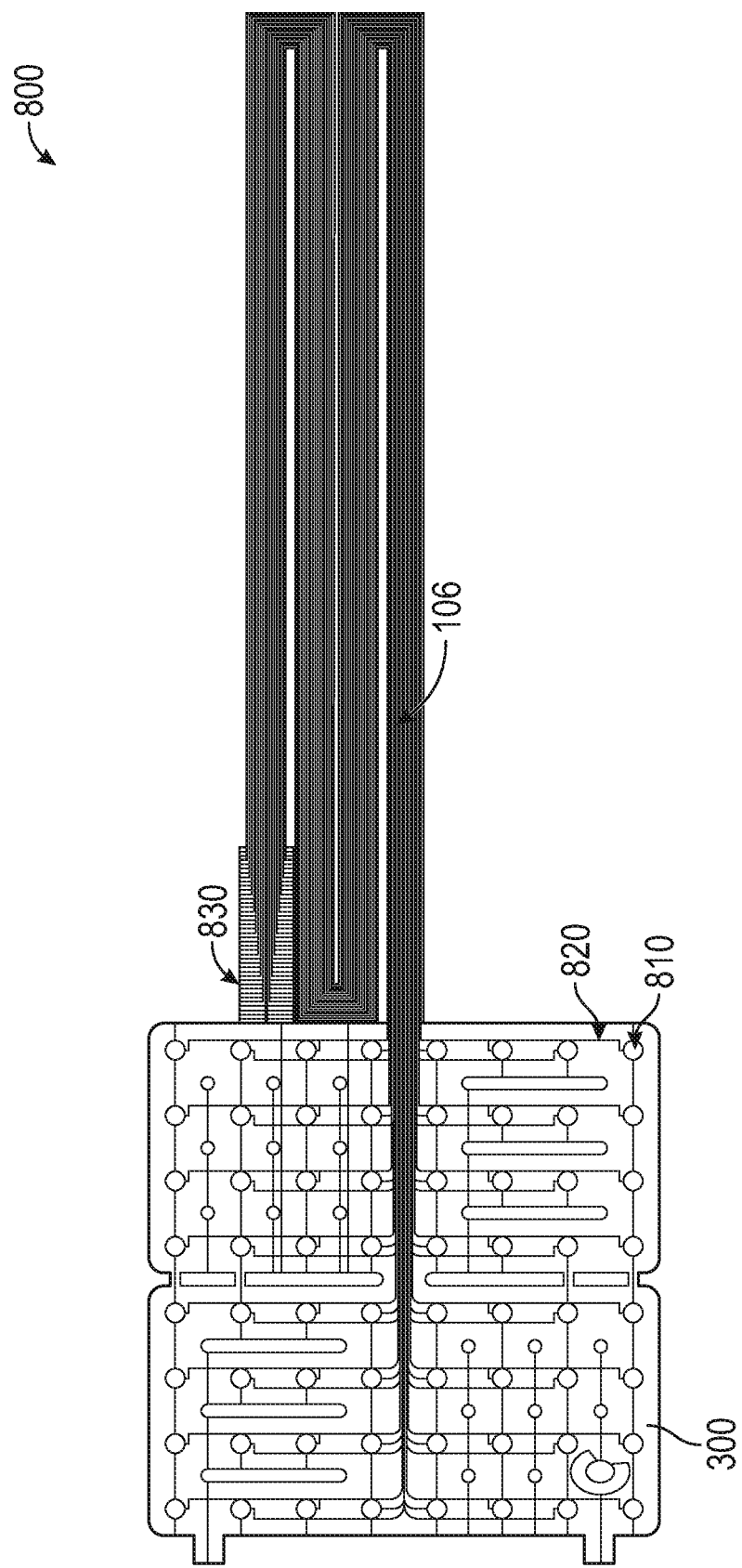

FIG. 8 shows another exemplary configuration 800 of the electrode array assembly 108 according to an embodiment of the present disclosure.

Figure 9:
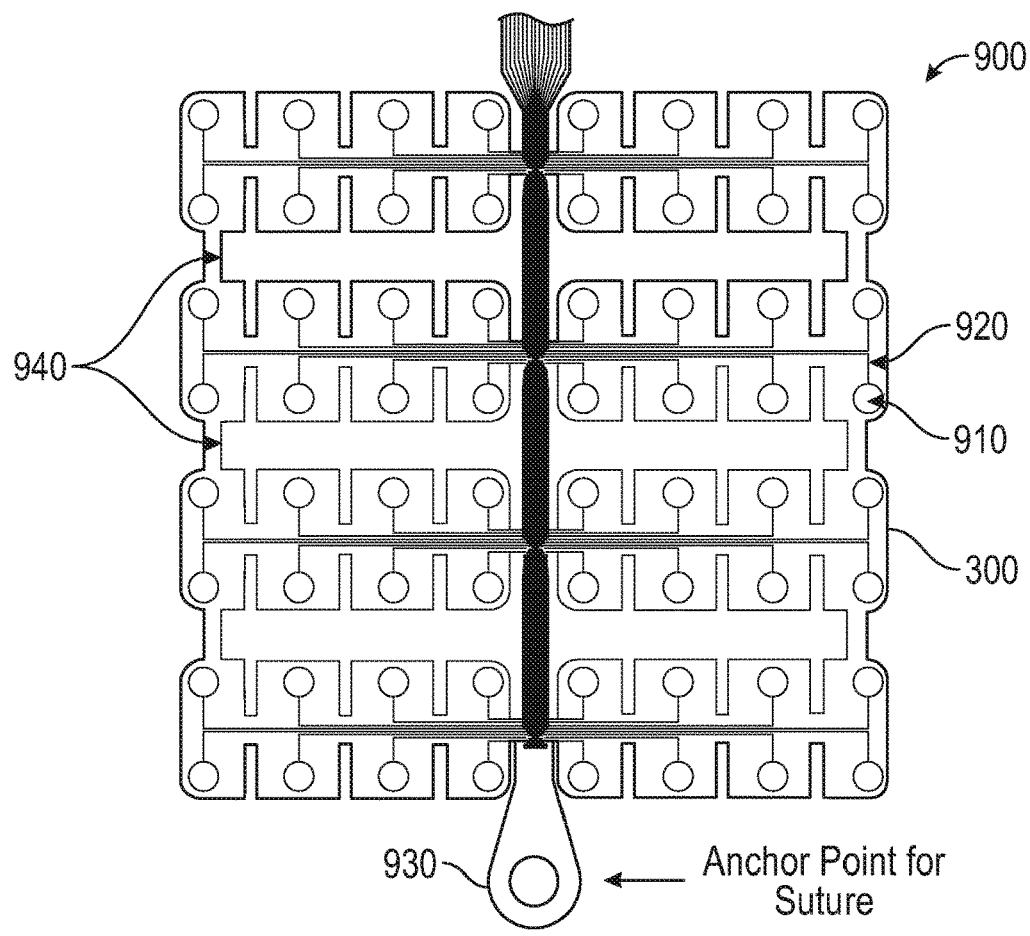

FIG. 9 shows another exemplary configuration 900 of the electrode array assembly 108 according to an embodiment of the present disclosure.

Figure 10:
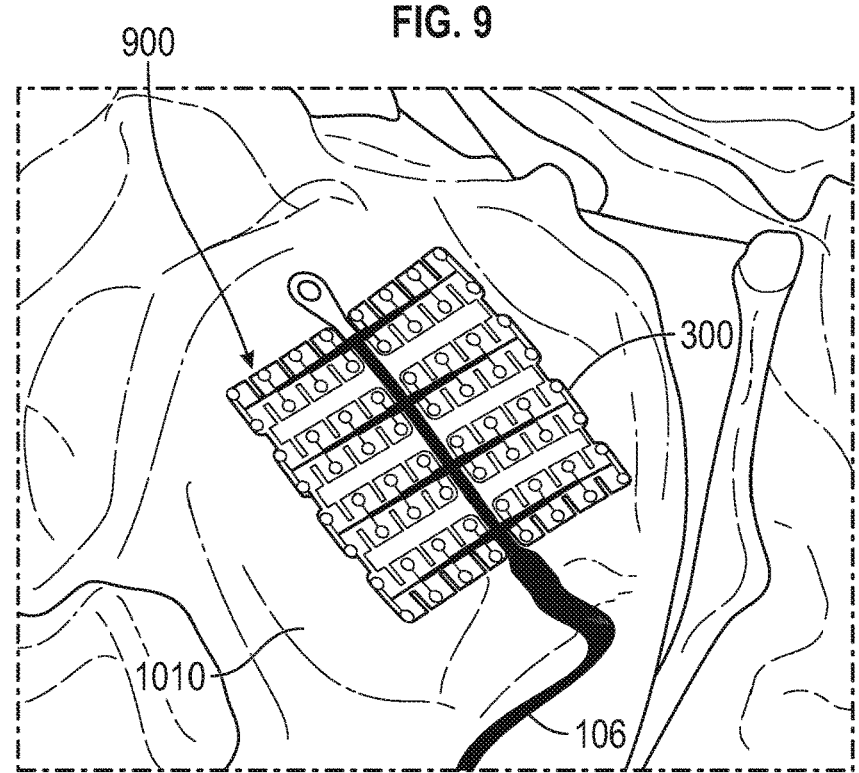

FIG. 10 shows the exemplary configuration 900 of the electrode array assembly 108 in contact with exterior biological tissue 1010 of a patient's heart, according to an embodiment of the present disclosure.

Figure 11A:
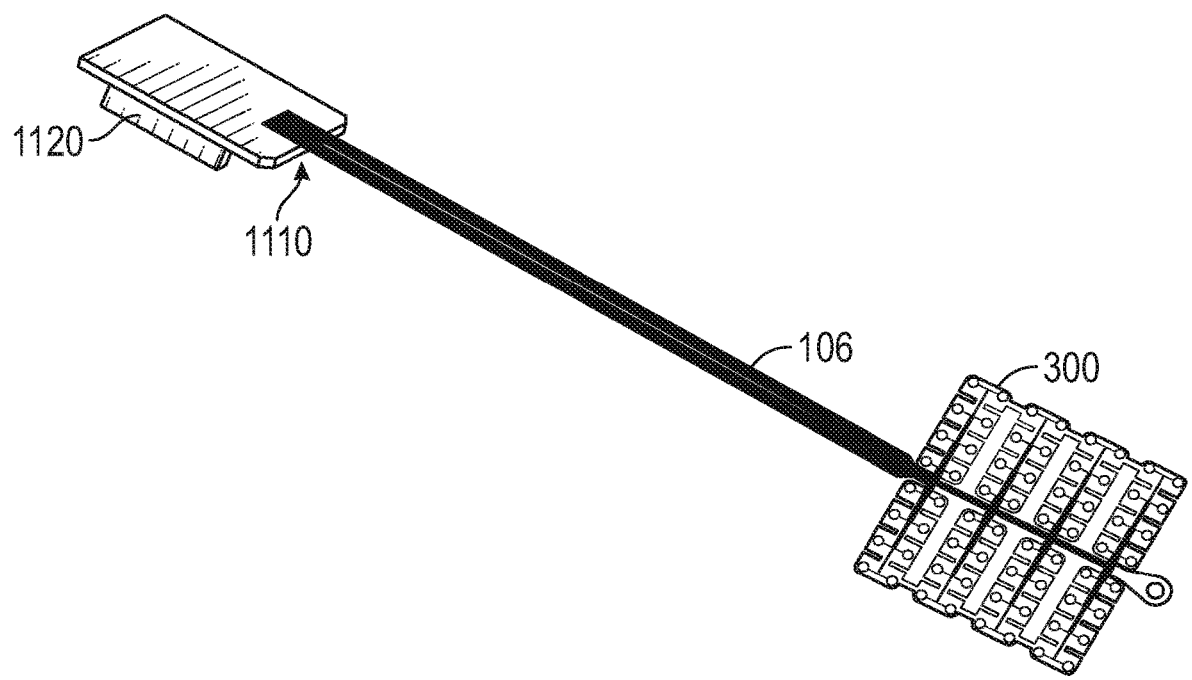

FIG. 11A shows exemplary electrical connections associated with the configuration 900 of the electrode array assembly 108 according to an embodiment of the present disclosure.

Figure 11B:
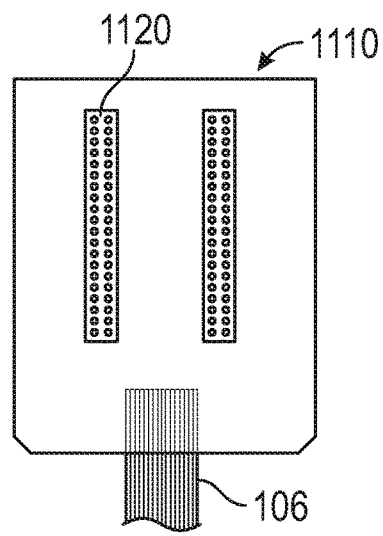

FIG. 11B shows an enlarge view of the printed circuit board 1110 from FIG. 11A according to an embodiment of the present disclosure.

Figure 12B:
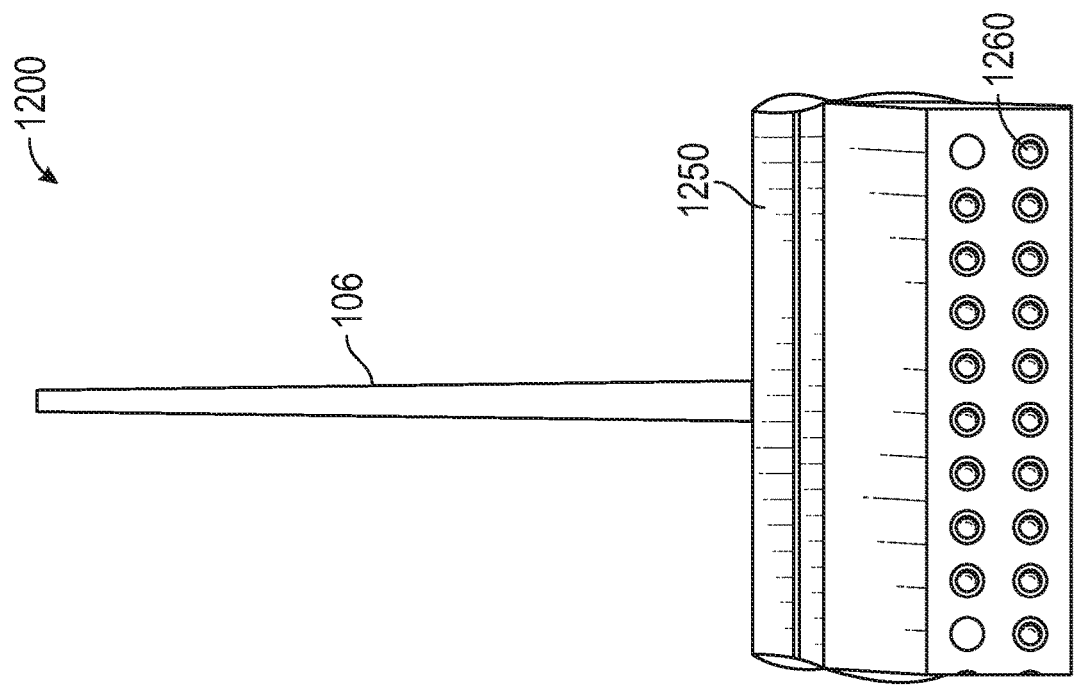
Figure 12A:
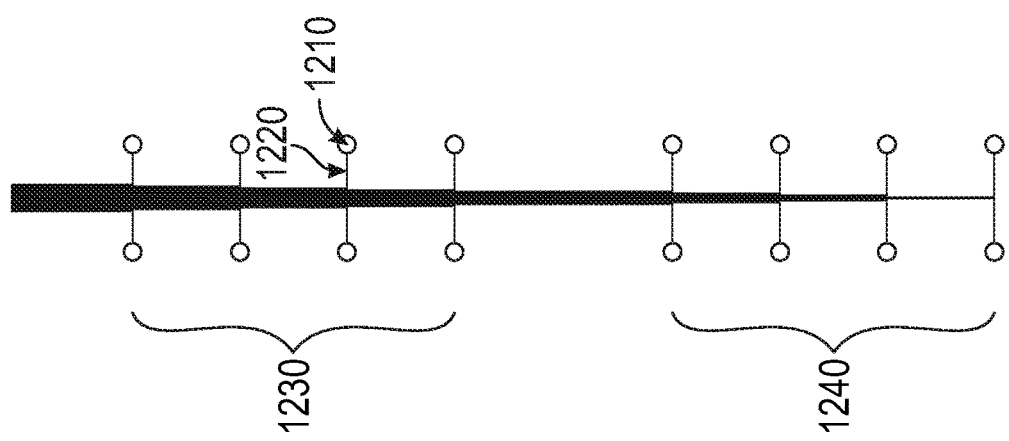

FIG. 12A shows another exemplary configuration 1200 of the electrode array assembly 108 according to an embodiment of the present disclosure.

FIG. 12B shows a proximal end of the flexible ribbon cable 106, according to an embodiment of the present disclosure.

Figure 13:
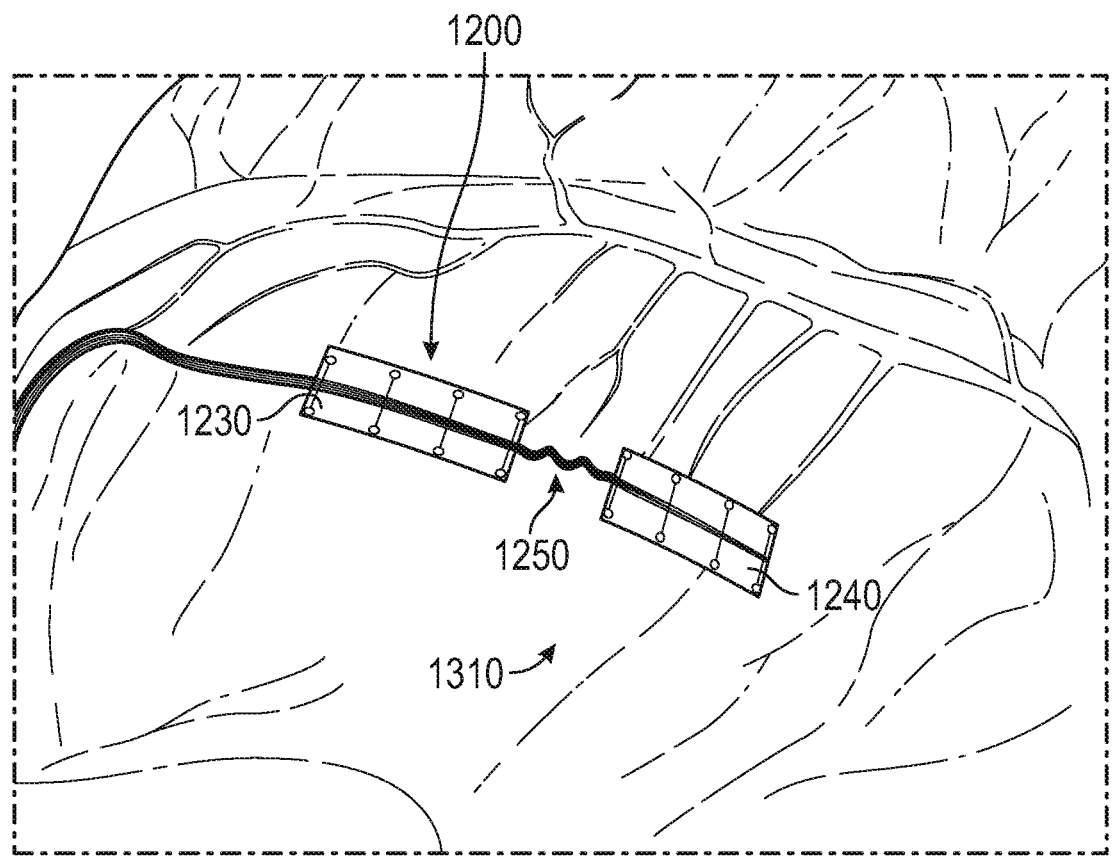

FIG. 13 shows the exemplary configuration 1200 of the electrode array assembly 108 in contact with exterior biological tissue 1310 of a patient's heart, according to an embodiment of the present disclosure.

Figure 14A:
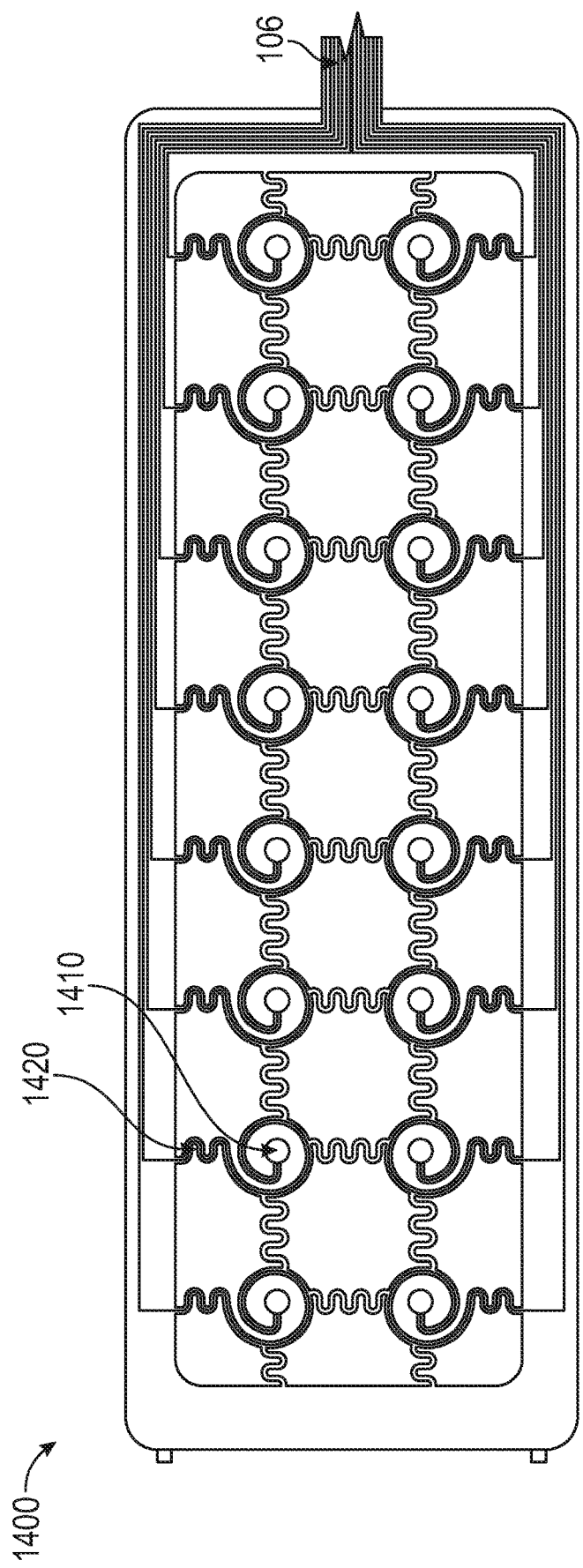

FIG. 14A shows another exemplary configuration 1400 of the electrode array assembly 108 according to an embodiment of the present disclosure.

Figure 14B:
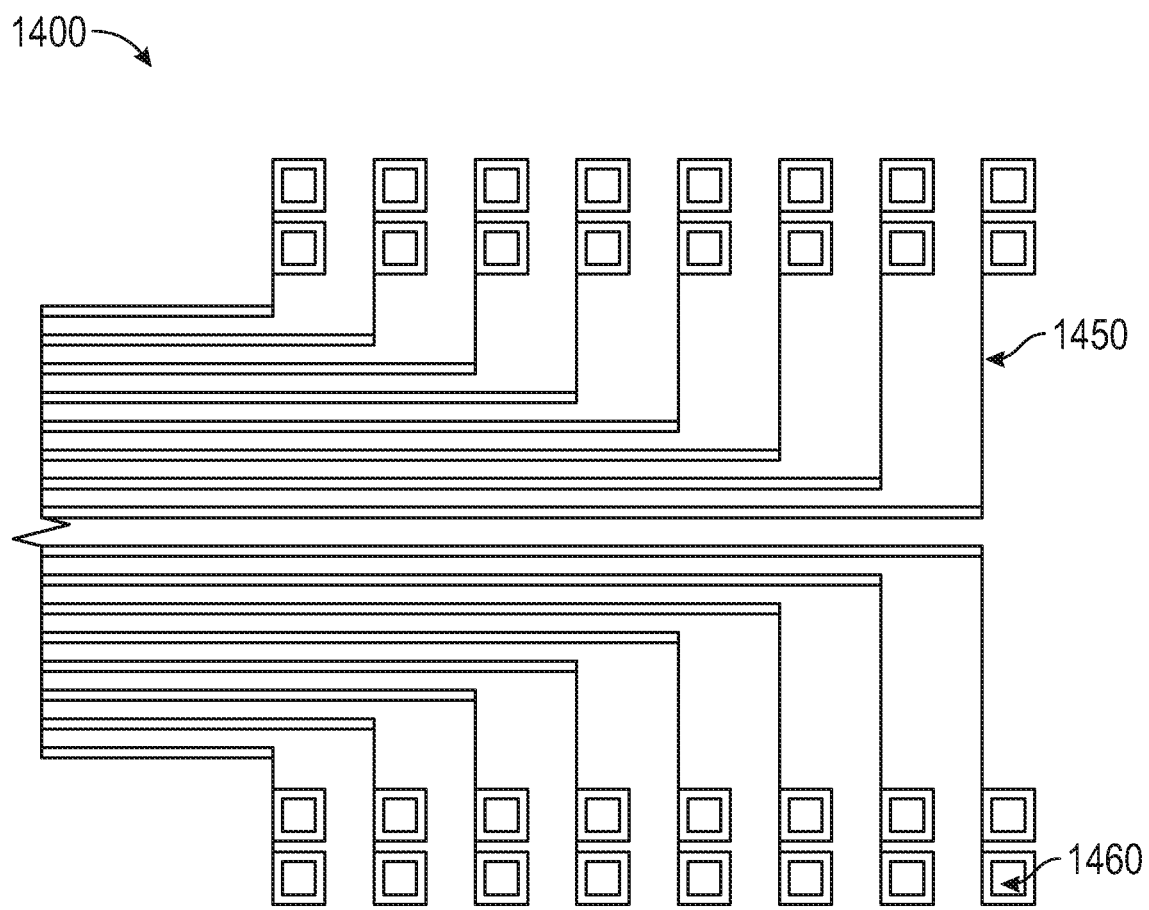

FIG. 14B shows a proximal end of the flexible ribbon cable 106, according to an embodiment of the present disclosure.

FIG. 15 shows another view of the exemplary electrode array assembly 108 of configuration 1400.

Figure 16:
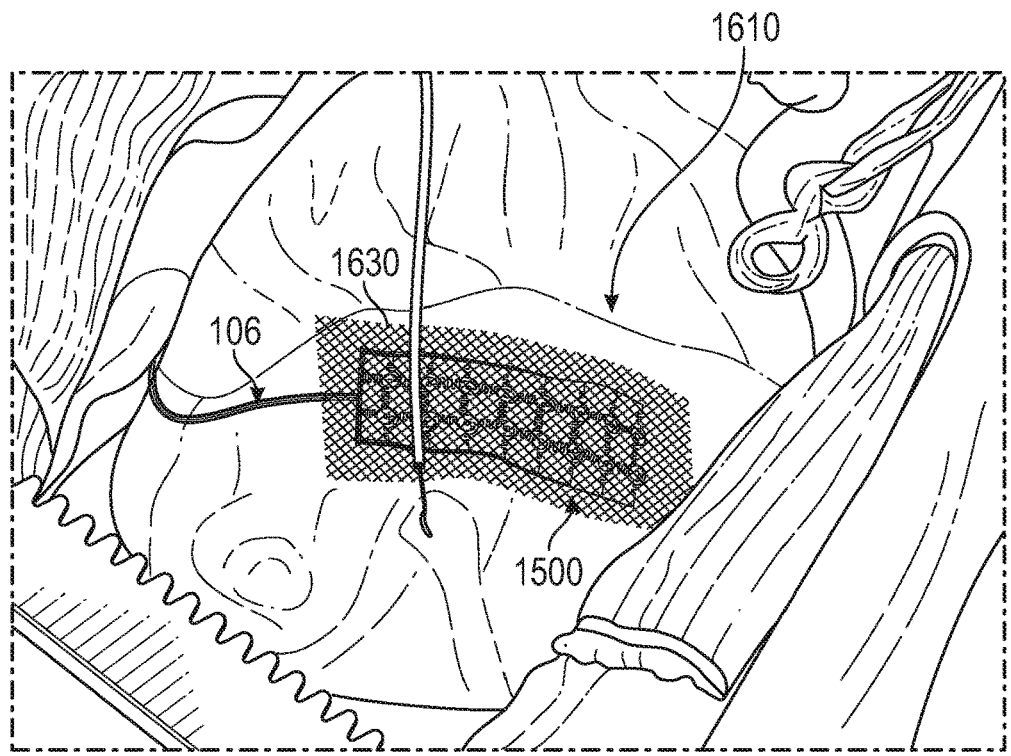

FIG. 16 shows the exemplary configuration 1500 of the electrode array assembly 108 in contact with exterior biological tissue 1610 of a patient's heart, according to an embodiment of the present disclosure.

Figure 17:
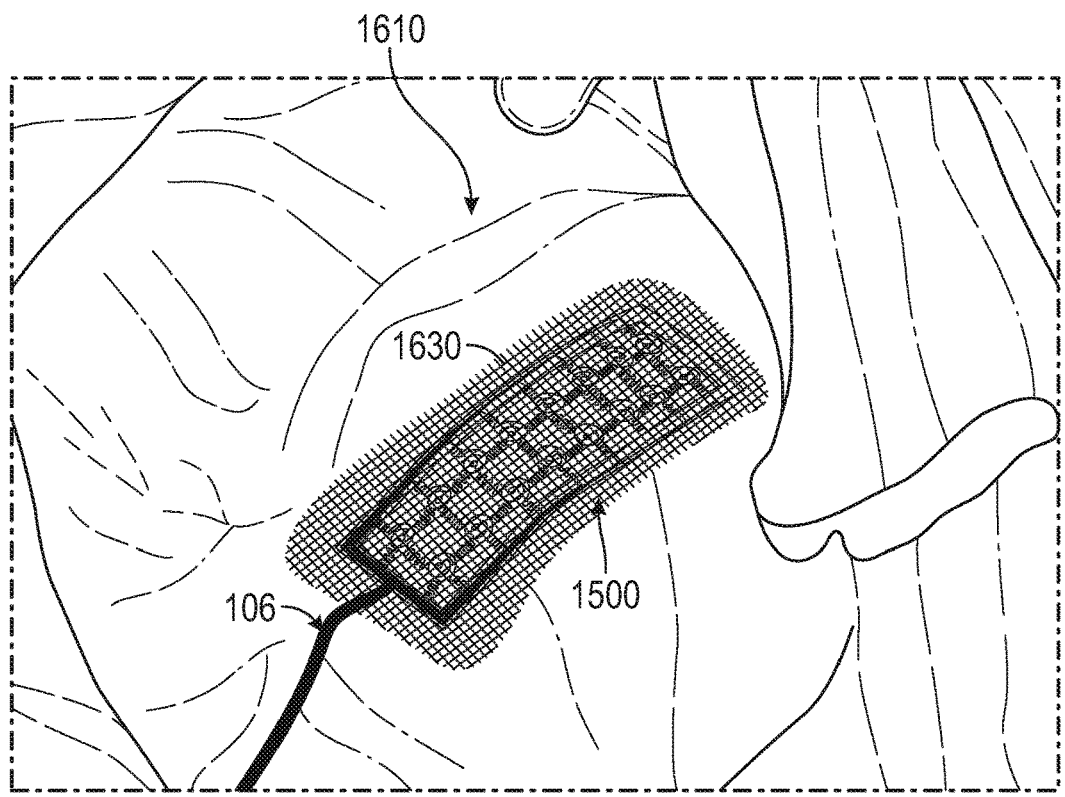

FIG. 17 shows another view of the exemplary configuration 1500 with the electrode array substrate 300 attached to the flexible mesh carrier 1630 in contact with exterior biological tissue 1610 of a patient's heart.

Figure 18:
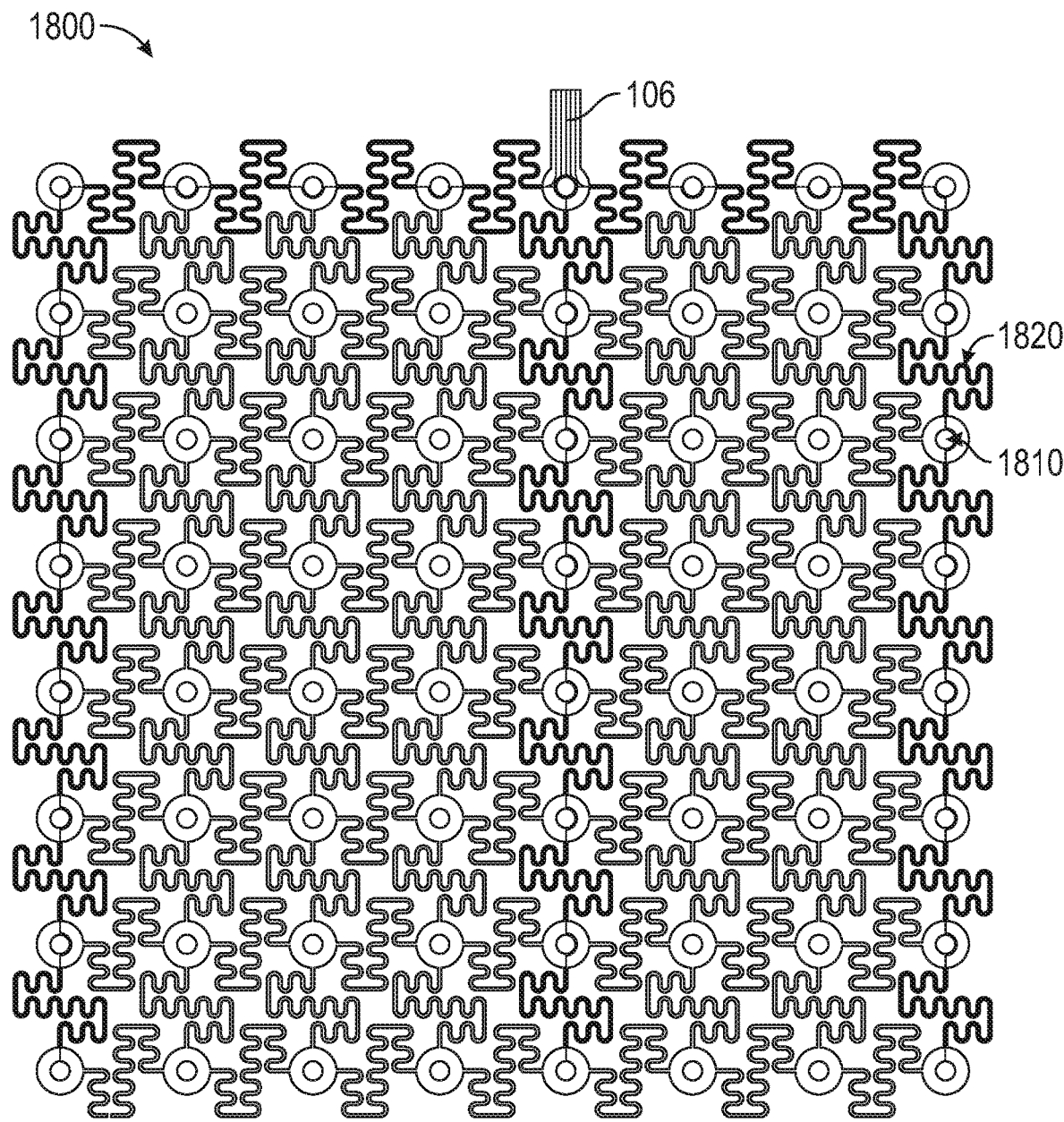

FIG. 18 shows another exemplary configuration 1800 of the electrode array assembly 108 according to an embodiment of the present disclosure.

Figure 19B:
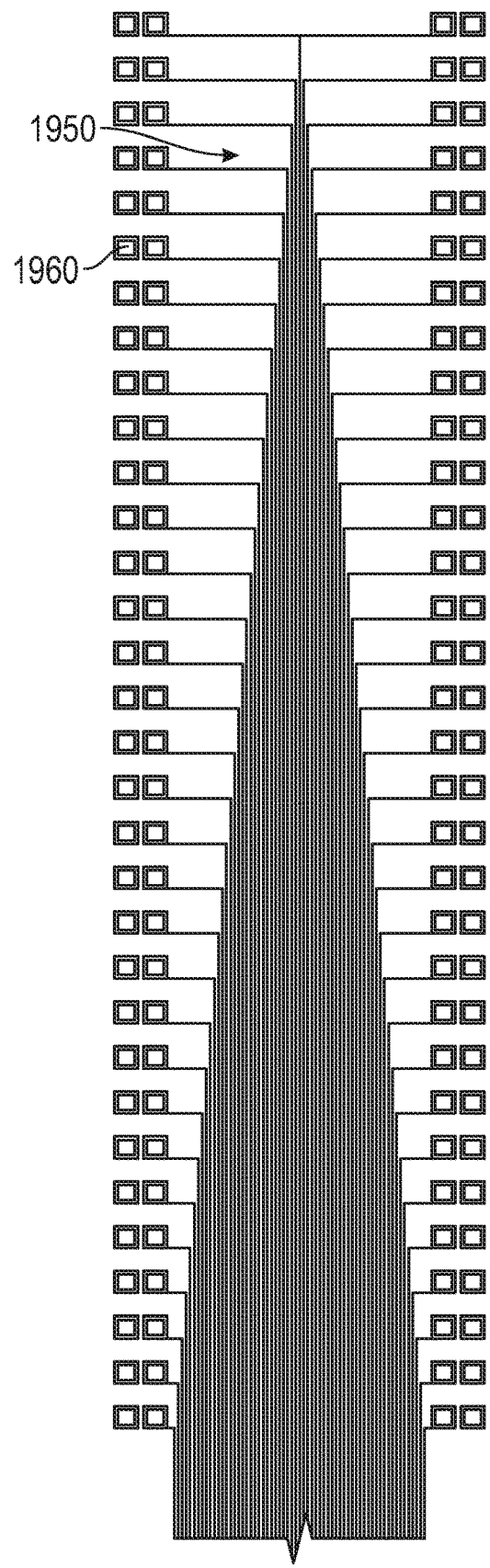
Figure 19A:
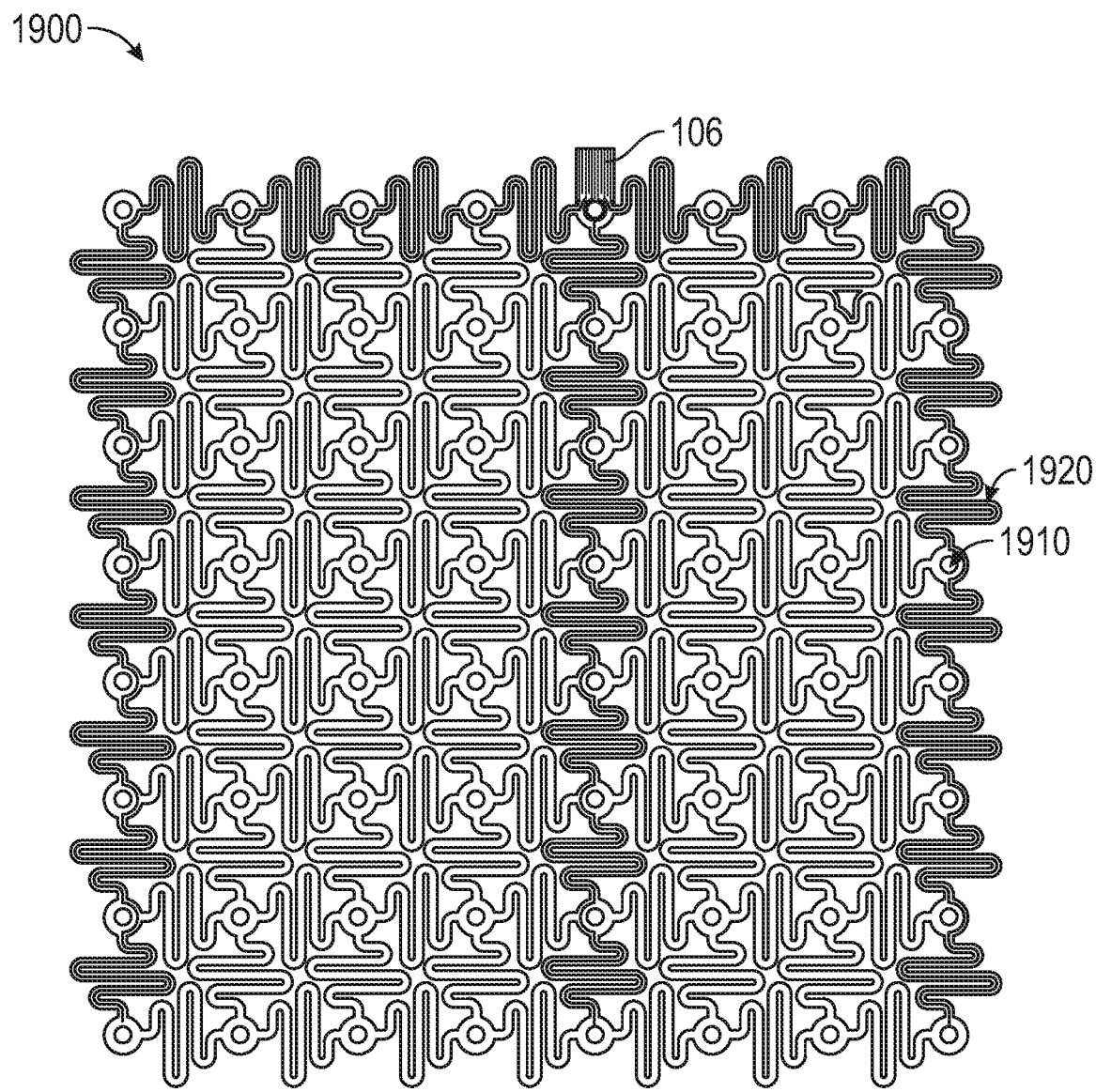

FIG. 19A shows another exemplary configuration 1900 of the electrode array assembly 108 according to an embodiment of the present disclosure.

FIG. 19B shows a proximal end of the flexible ribbon cable 106 according to an embodiment of the present disclosure.

Figure 20:
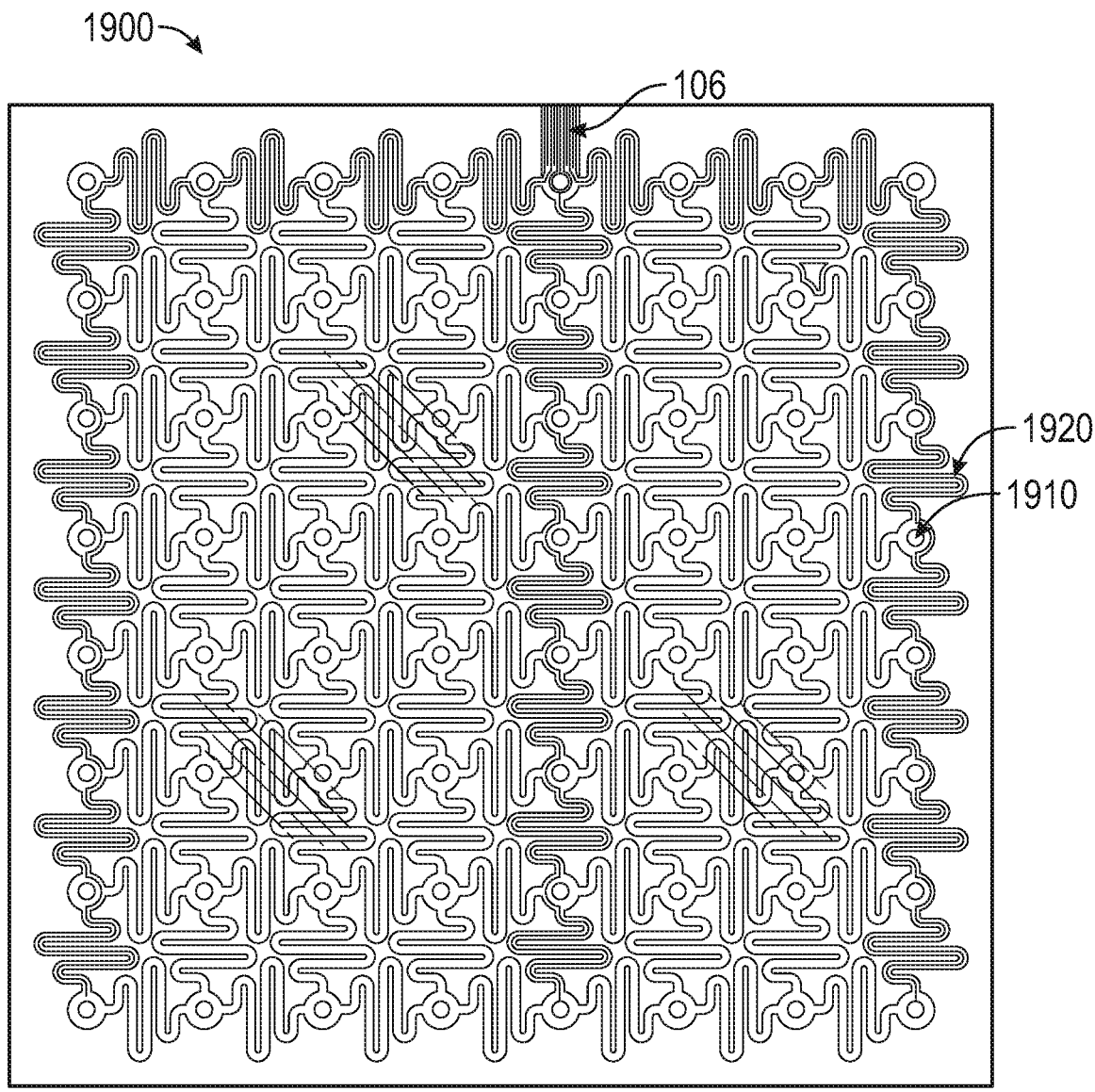

FIG. 20 shows another view of the exemplary electrode array assembly 108 of configuration 1900.

Figure 21:
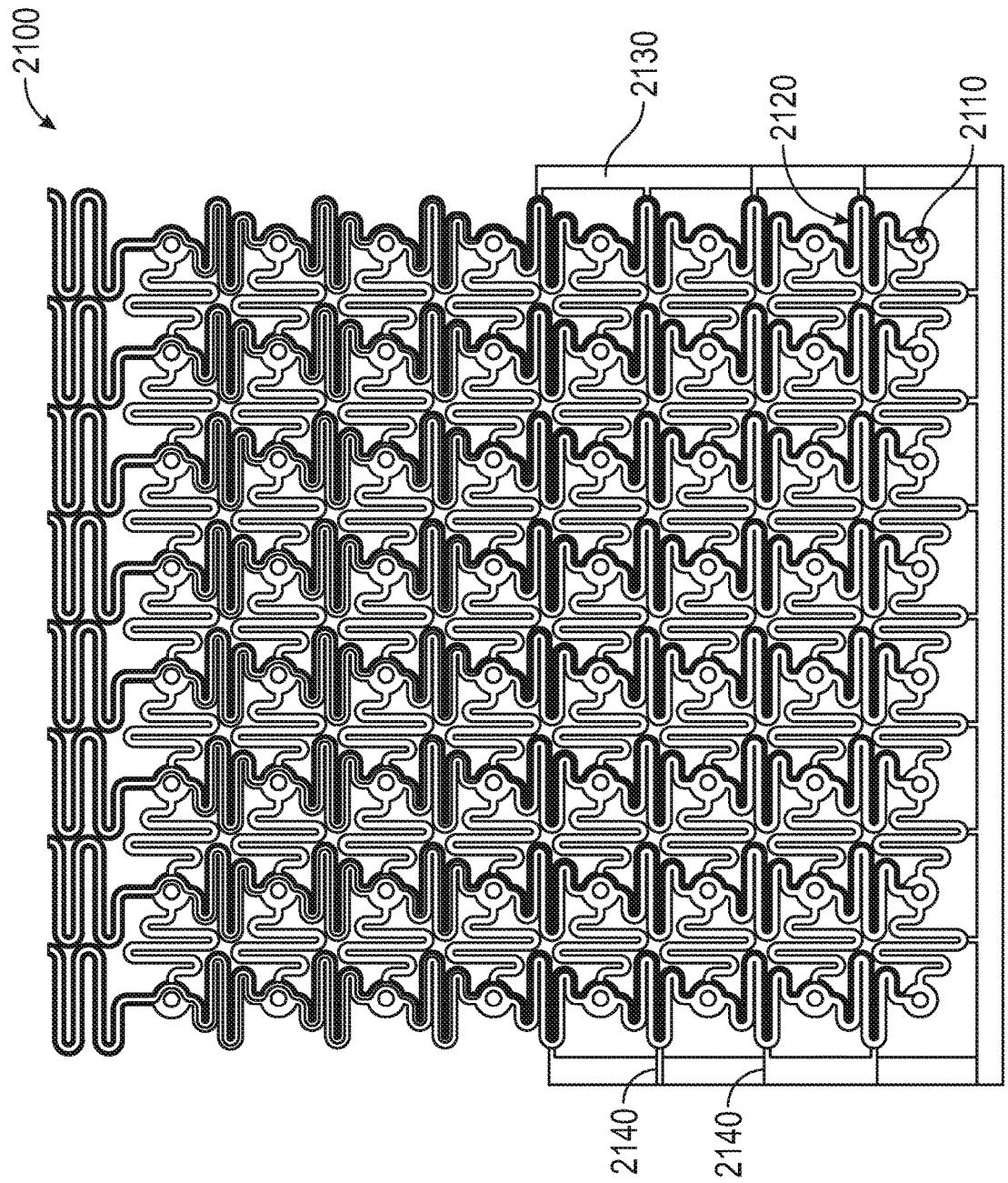

FIG. 21 shows another exemplary configuration 2100 of the electrode array assembly 108 according to an embodiment of the present disclosure.

Figure 22:
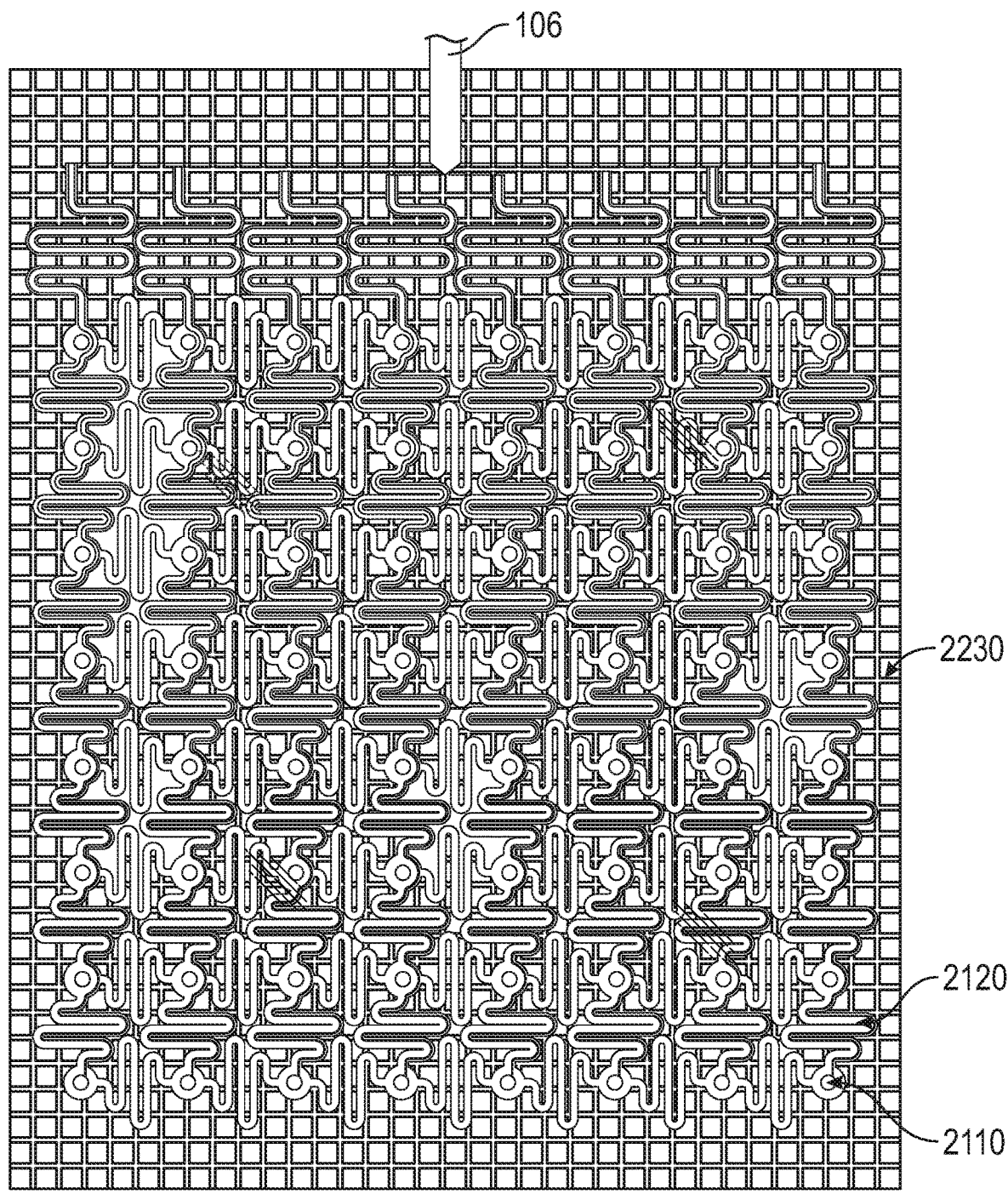

FIG. 22 shows the exemplary configuration 2100 of the electrode array assembly 108, according to an embodiment of the present disclosure.

Figure 23:
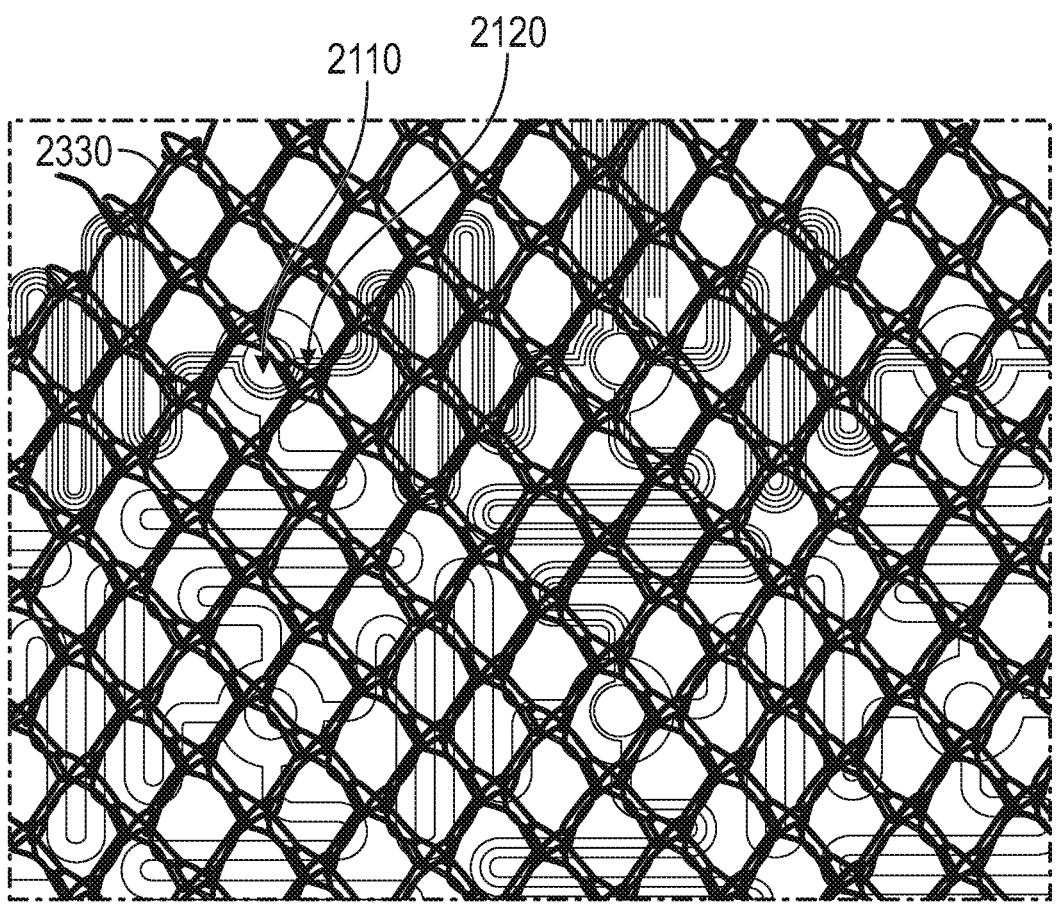

FIG. 23 shows another view of the exemplary configuration 2100 with the electrode array substrate 300 attached to a flexible woven mesh carrier 2230 according to an embodiment of the present disclosure.

Figure 24:
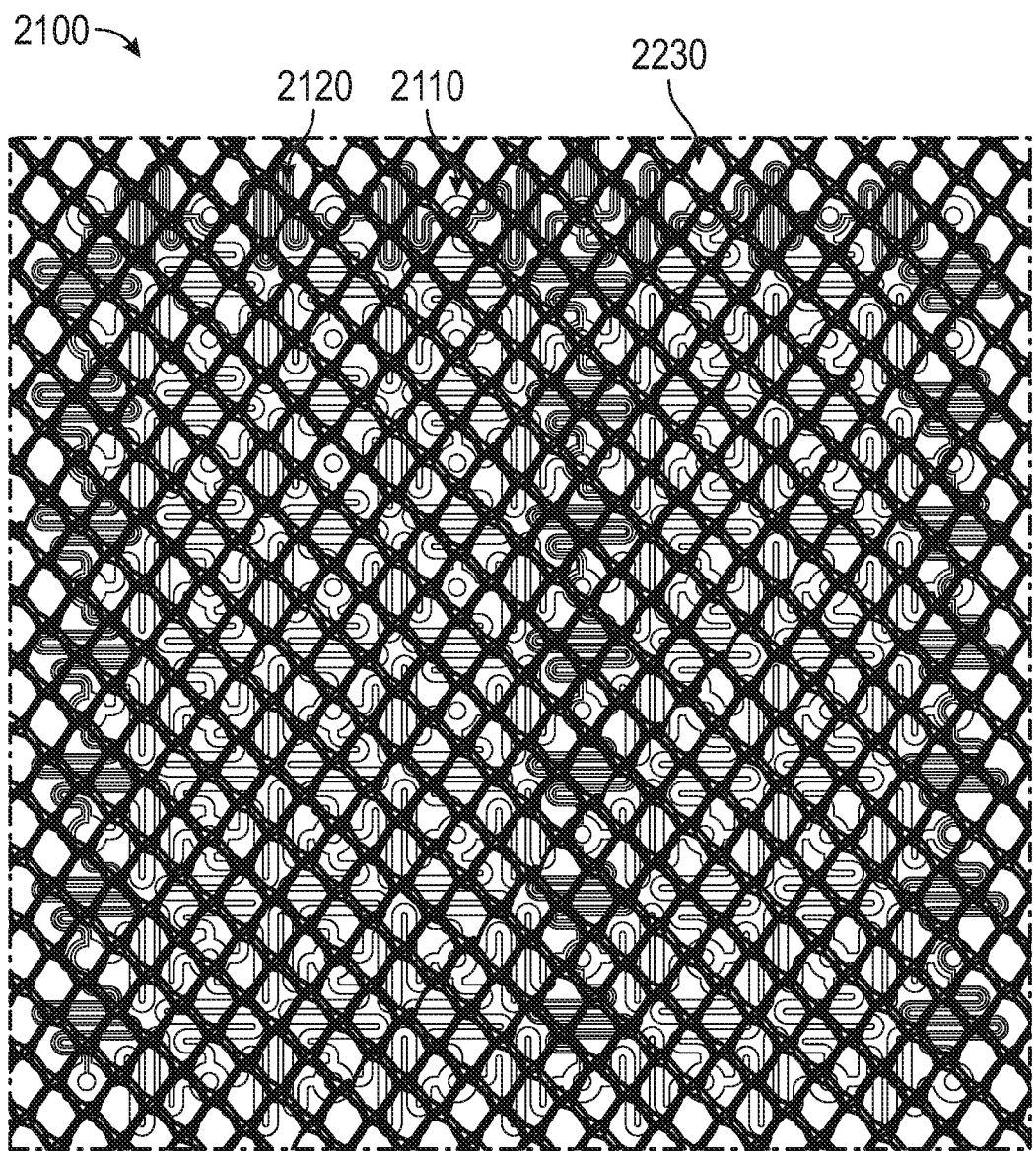

FIG. 24 shows another view of the exemplary configuration 2100 with the electrode array substrate 300 attached to the flexible woven mesh carrier 2230 according to an embodiment of the present disclosure.

Figure 25:
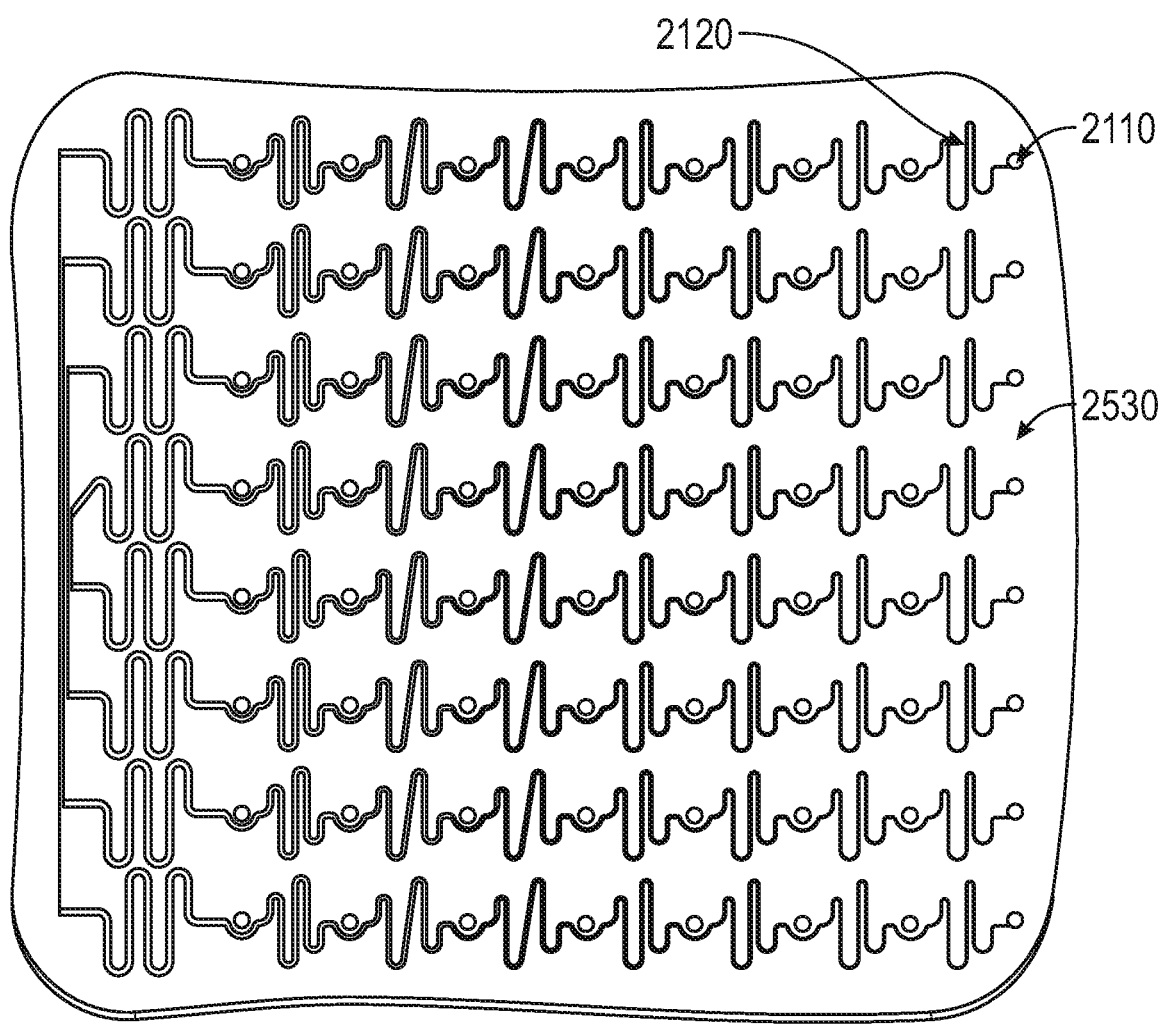

FIG. 25 shows another view of the exemplary configuration 2100 with the electrode array substrate 300 attached to a flexible and stretchable silicone carrier 2530 according to an embodiment of the present disclosure.

Figure 26:
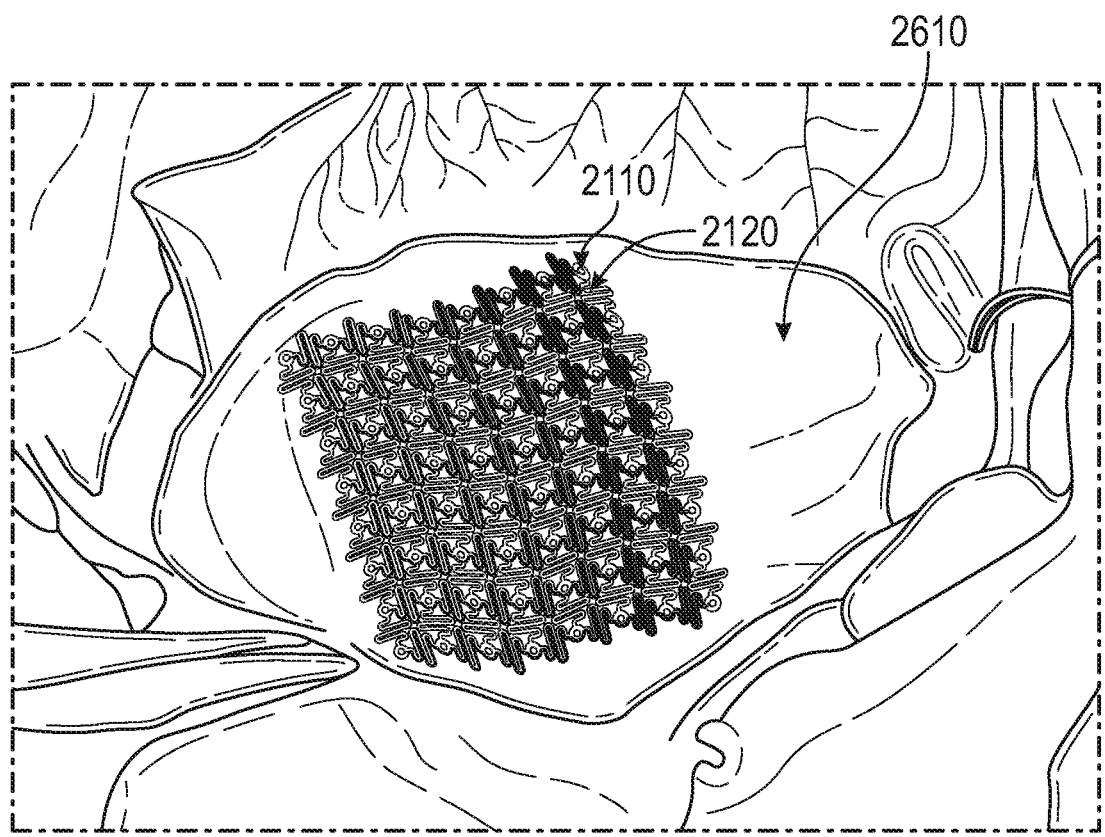

FIG. 26 shows the exemplary configuration 2100 of the electrode array assembly 108 in contact with exterior biological tissue 2610 of a patient's heart, according to an embodiment of the present disclosure.

Figure 27:
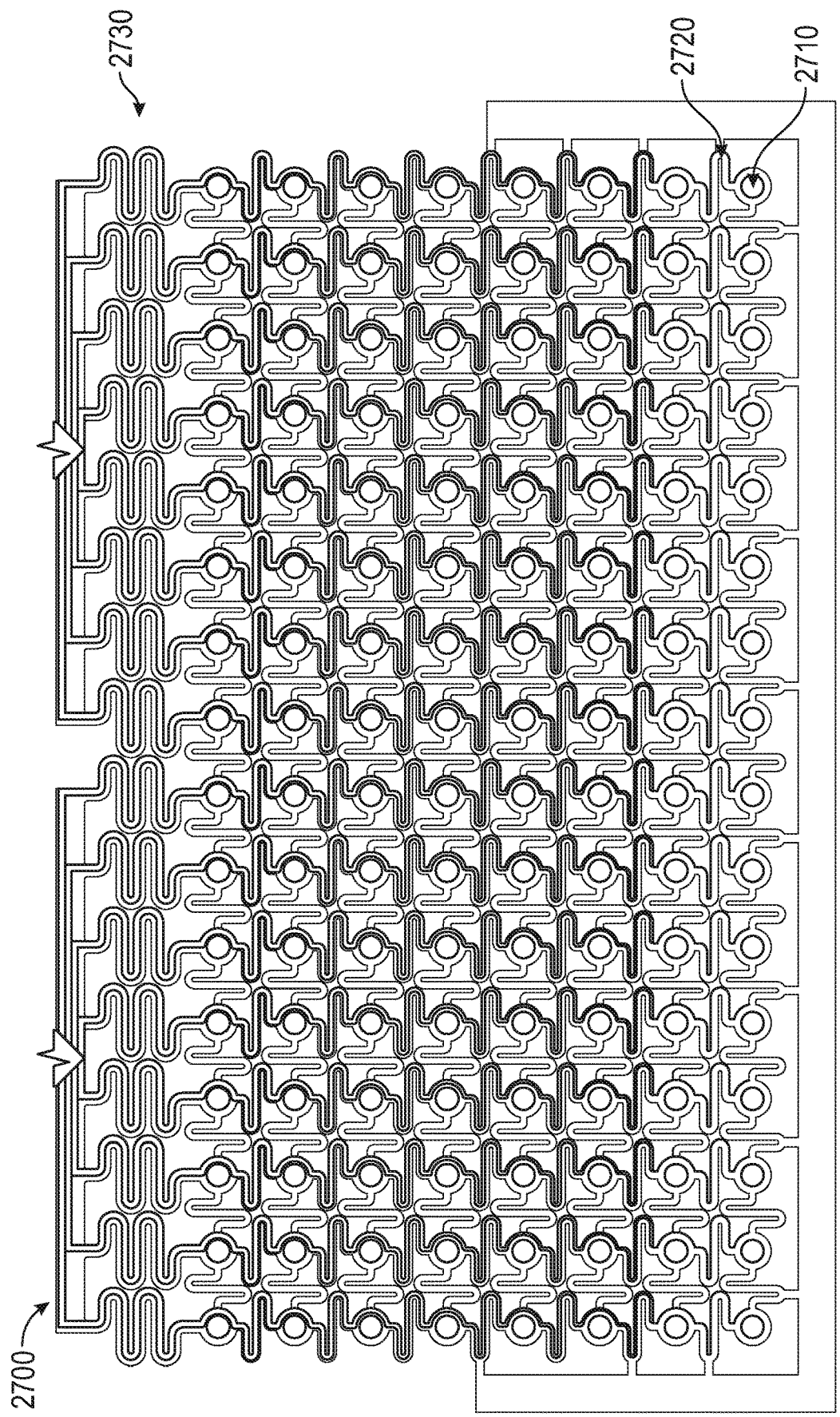

FIG. 27 shows another exemplary configuration 2700 of the electrode array assembly 108 according to an embodiment of the present disclosure.

Figure 28:
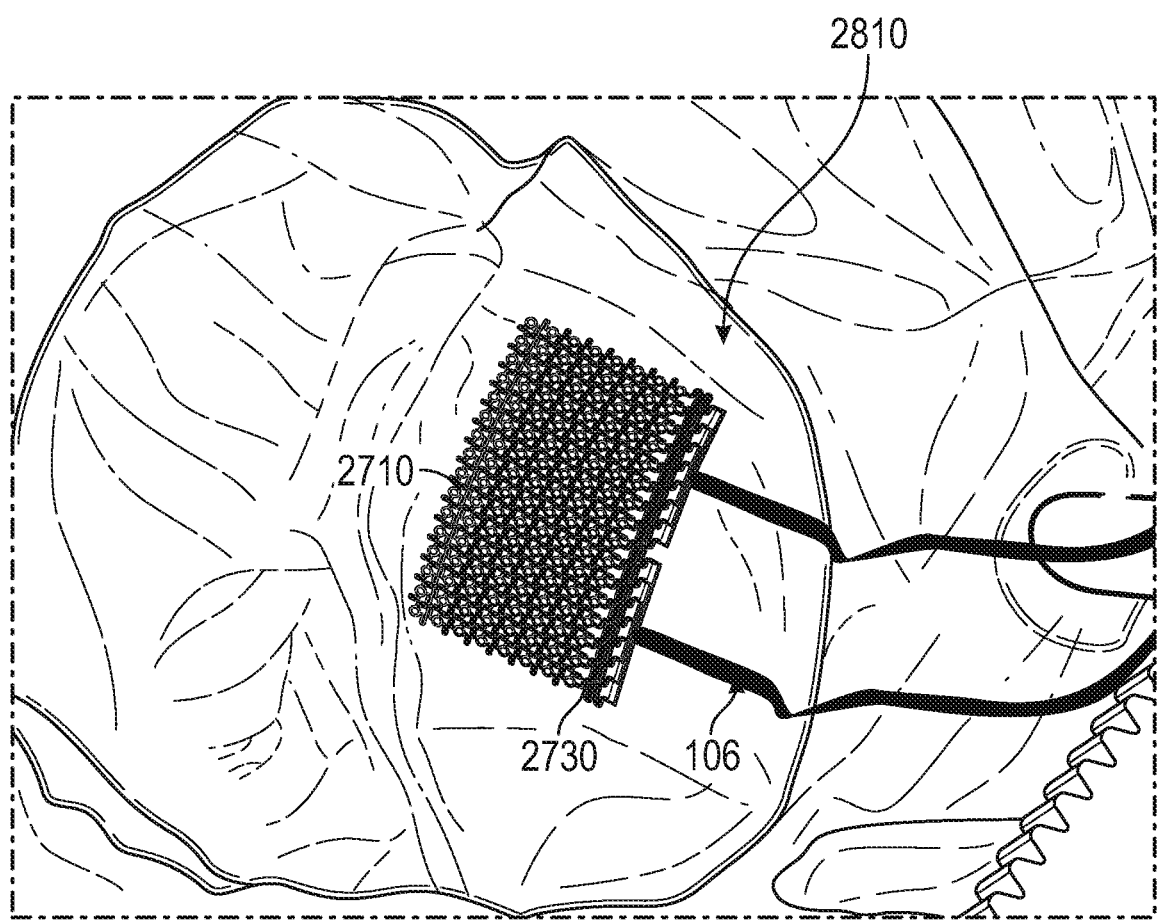

FIG. 28 shows the exemplary configuration 2700 of the electrode array assembly 108 in contact with exterior biological tissue 2810 of a patient's heart, according to an embodiment of the present disclosure.

Figure 29:
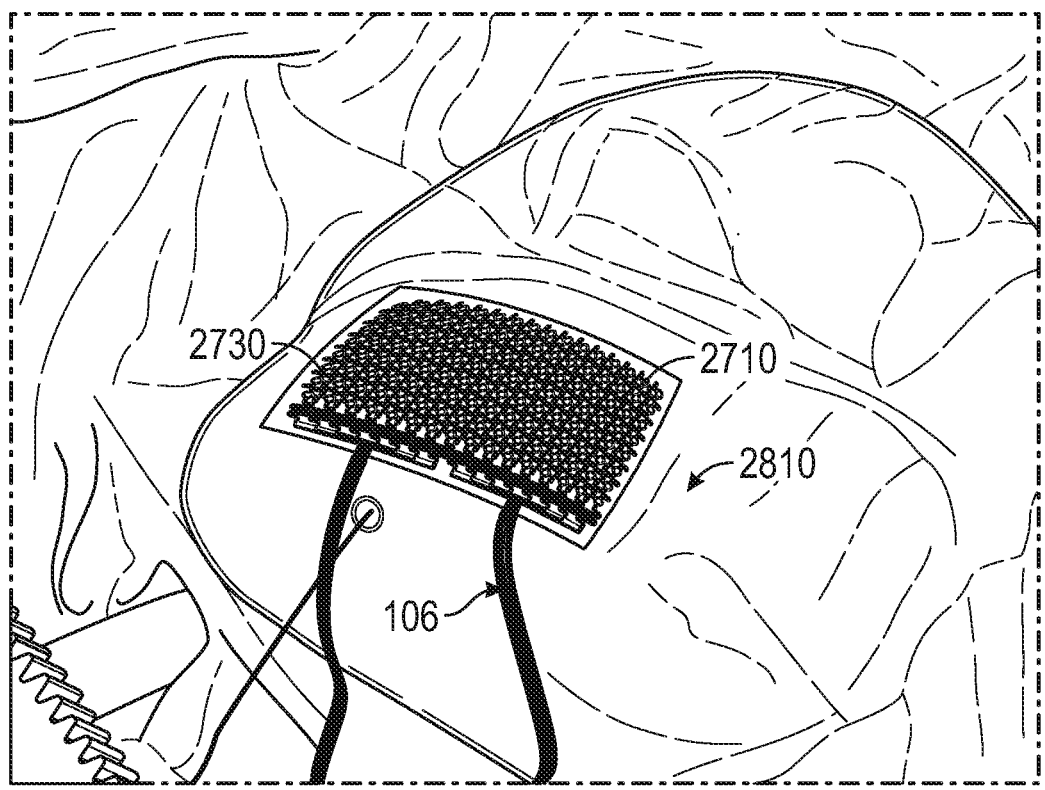

FIG. 29 shows another view of the exemplary configuration 2700 of the electrode array assembly 108 in contact with exterior biological tissue 2810 of a patient's heart, according to an embodiment of the present disclosure.

Figure 30:
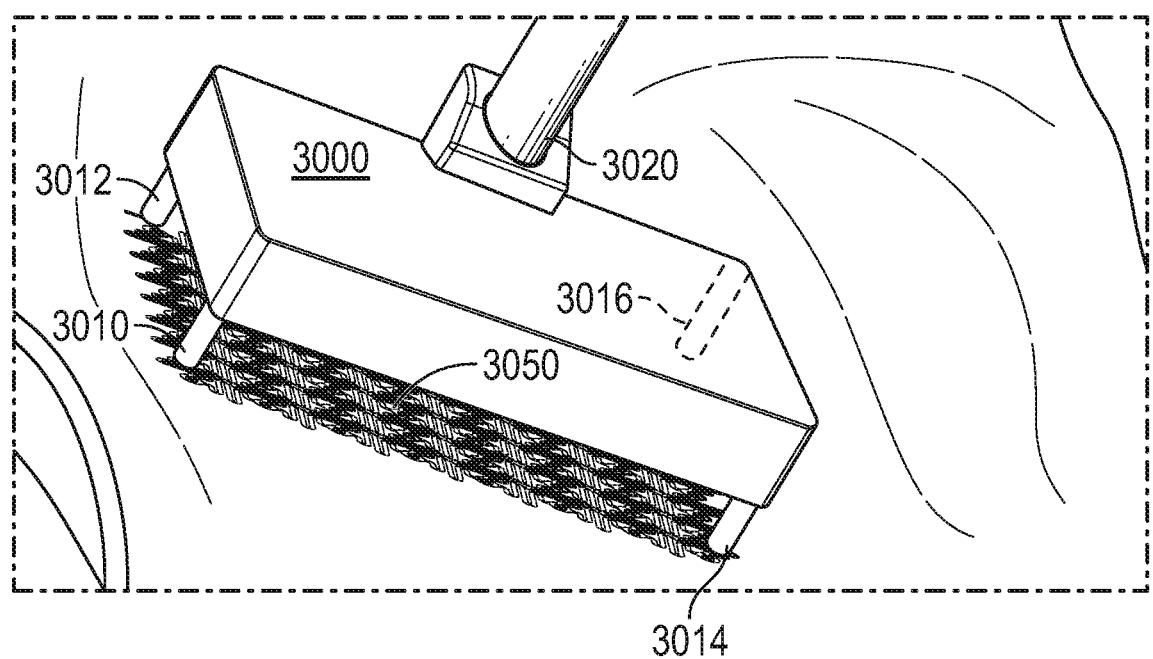

FIG. 30 shows an inserter 3000 for holding a flexible array 3050, according to an embodiment of the present disclosure.

Figure 31:
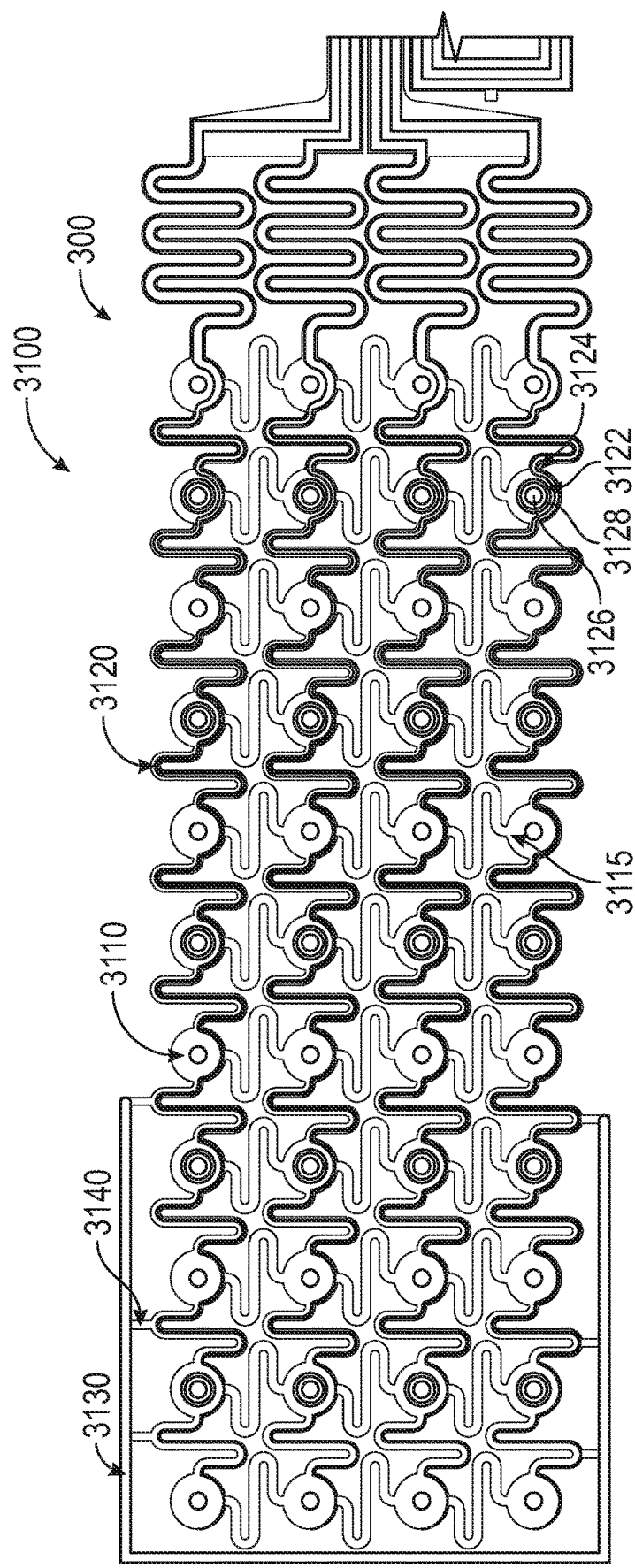

FIG. 31 is a top view of a flexible array having concentric electrodes, according to an embodiment of the present disclosure.

Figure 32:
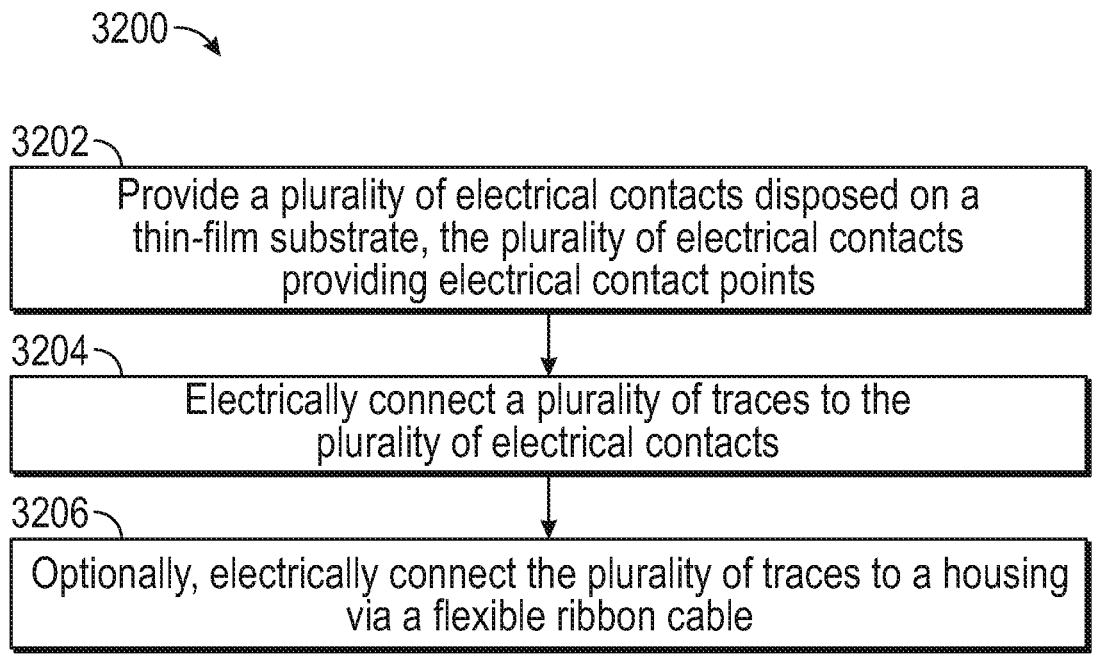

FIG. 32 is a flowchart of a process for assembling a flexible electrode array system, according to an embodiment of the present disclosure.

These Figures may be better understood by reference to the following detailed description.

DETAILED DESCRIPTION

It is to be understood that the following disclosure provides many different embodiments, or examples, for implementing different features of the disclosure. Specific examples of components and arrangements are described below to simplify the present disclosure. These are, of course, merely examples and are not intended to be limiting. Various features may be arbitrarily drawn in different scales for simplicity and clarity.

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways.

This detailed description discloses systems and methods for sensing neural impulses generated by the body. By bringing electrodes into close contact with the nerves, the electrical signals produced by the nerves can be recorded and processed for research, diagnosis, and for interventional planning. Additionally, various embodiments of the present disclosure may include stimulation electrodes in addition to or as an alternative to recording electrode. The stimulation electrodes can be used to stimulate the tissues (e.g., nerves and/or muscles) in proximity to the electrodes. Such stimulation may be performed for diagnostic purposes as well as for therapeutic purposes. Embodiments of the present disclosure may be utilized to monitor and interact with a variety of tissues.

The human nervous system includes a complex network of neurological structures that extend throughout the body. The brain interconnects with the spinal cord which branches into the brachial plexus near the shoulders and the lumbar plexus and sacral plexus in the lower back. The vagus nerve interfaces with the autonomous control of the heart, lungs, and digestive tract. The limb peripheral nerves of the arms extend distally from the brachial plexus down each arm. Similarly, the limb peripheral nerves of the legs extend distally from the lumbar plexus and sacral plexus. The peripheral nervous system provides an interface between the central nervous system and other anatomical structures like the muscular system.

Because of differences in the tissue at the target site for an electrode array, the insertion force may be modulated so that the surgeon can manage the insertion smoothly and reduce the likelihood of damaging the individual electrodes/probes and their associated circuitry and the target tissue. While some tissues, such as brain tissue may be relatively soft, yielding more easily to the insertion of electrodes, other tissues are more difficult. For example, cardiac tissues which are largely muscular can provide significantly more resistance the insertion or implantation of electrodes. Embodiments of the present disclosure may provide electrode contacts for connection to penetrating electrodes for mechanical anchoring and/or depth electrode interfacing. Electrode contacts may also be referred to as electrode sites or electrical contacts. In certain cases, the electrode contacts may be implemented using bond pads or affixed to bond pads. As referred herein, bond pads (or "bondpads") may take the form of electrode sites, electrode contacts, or designated surface areas or portions of a substrate. For example, a bond pad may be a designated surface area or a portion of a printed circuit board or die. In some cases, the bond pad may be a portion of a thin-film based substrate made from polyimide, parylene, or silicone with embedded conductors (e.g., gold, platinum, etc.).

Figure 1:
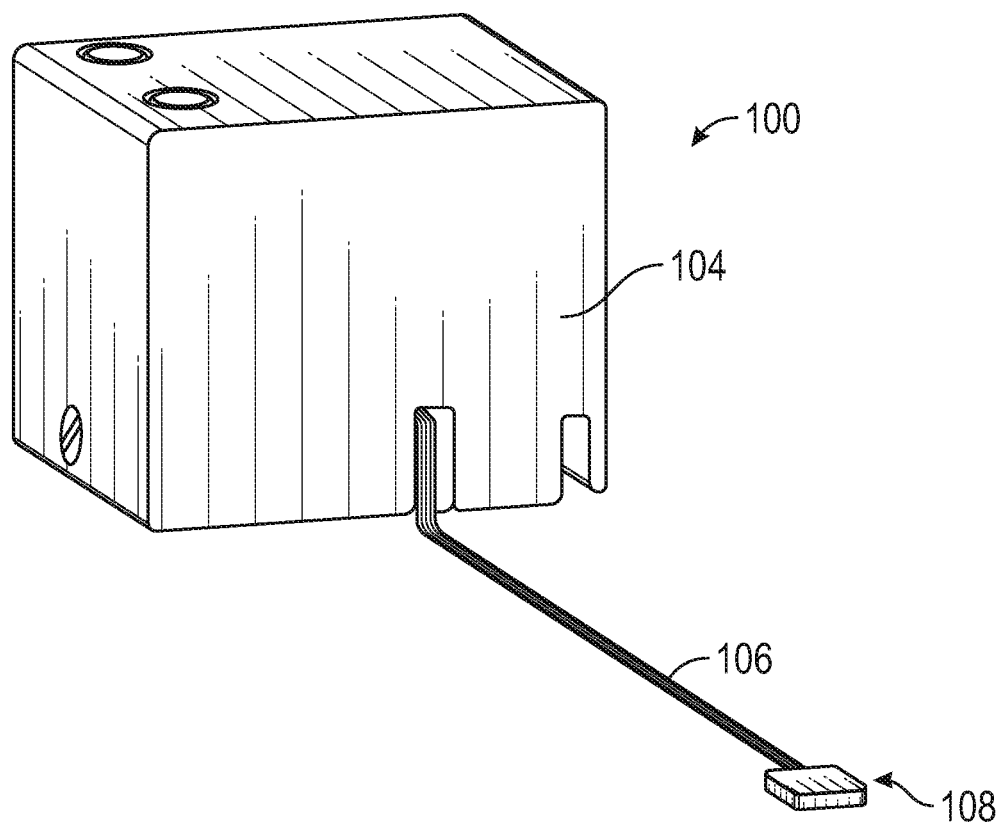
FIG. 1 is a perspective view of an electrode array system according to various embodiments of the present disclosure.

Turning now to the drawings, FIG. 1 is a perspective view of an electrode array system 100 according to the various embodiments of the present disclosure. The electrode array system 100 may comprise a housing 104 containing various electronic circuits and components. A flexible ribbon cable 106 may connect the electronic circuits and components in the housing 104 to an electrode array assembly 108. In various embodiments, the flexible ribbon cable 106 may include wires or thin-film conductive traces insulated with thin-film dielectrics to provide the electrical connections between the housing 104 and the electrode array assembly 108. The electrical connections provided by the wires or thin-film conductive traces may enable provision of power, communication of signals to and from the electronic circuits and components in the housing 104 to the electrode array assembly 108. In various embodiments, the electronic circuits and components in the housing 104 may control operation of the electrode array assembly 108 through communication of the signals. Wires or thin-film conductive traces may also provide an electrical ground for the subject, and may be used as a reference when performing differential recording, or as a return path for current when stimulating tissue. The electrode array assembly 108 according to the present disclosure may include at least one, and preferably a plurality of probe electrode arrays.

Figure 2:
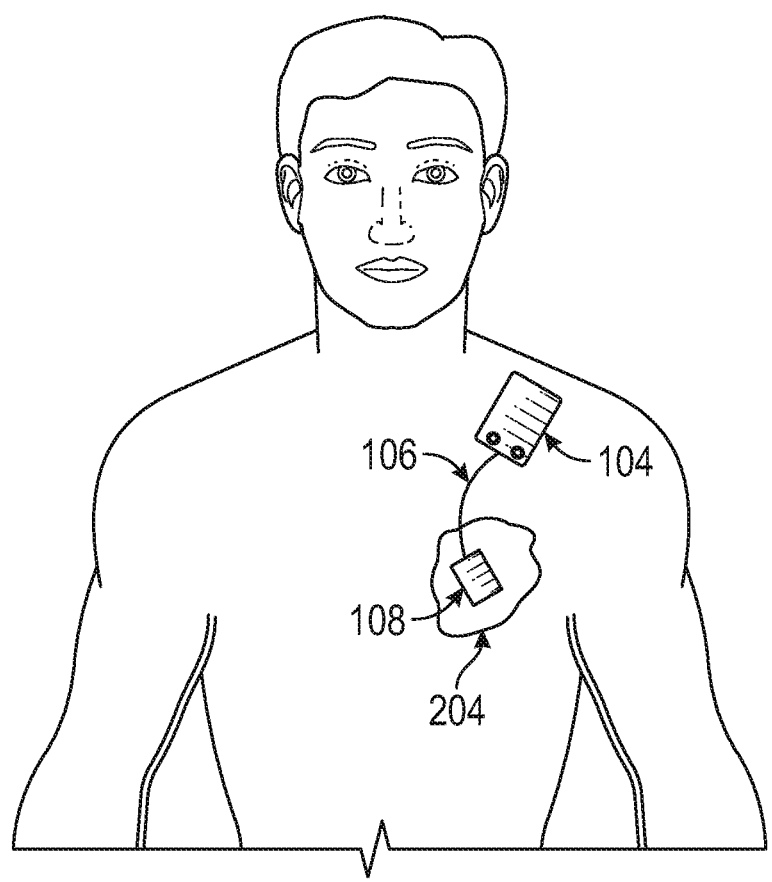
FIG. 2 is a top view of the electrode array system of FIG. 1 attached to a patient in a cardiac application of the system, according to various embodiments of the present disclosure.

FIG. 2 shows an exemplary application of the electrode array system 100. FIG. 2 is a top view of the electrode array system 100 attached to a patient in a cardiac application of the system 100, according to various embodiments of the present disclosure. A surgeon may couple the electrode array assembly 108 to an exterior surface of the heart 204, exposed during a cardiac operation or surgery. The housing 104 along with the electronics can be affixed to a location inside or outside the patient's body, with the wires or thin-film conductive traces extending between the housing 104 and the electrode array assembly 108. In various embodiments, the housing 104 may be integrated into the electrode array assembly 108 so that the electronic components and circuits contained in the housing 104 are positioned along with the electrode array assembly 108. Embodiments of the system 100 may be deployed in or on other parts of the body, in addition to those shown in FIG. 2.

Figure 3:
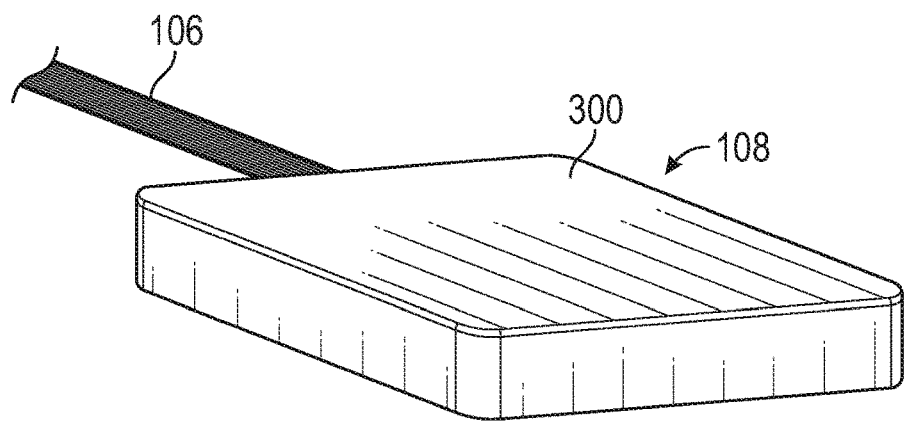
FIG. 3 is a perspective view of an electrode array assembly according to the present disclosure.

FIG. 3 is an enlarged view of the electrode array assembly 108 shown in FIG. 1. As shown, a distal portion of the flexible ribbon cable 106 may be connected to the electrode array assembly 108. The ribbon cable 106 may be designed to be flexible to allow the electrode array assembly 108 to be positioned freely within the radius defined by the length of the ribbon cable 106 relative to the electronics housing 104. This allows the electrode array assembly 108 to "float" with the contacted tissue during natural pulsation and/or shifting of the tissue within the patient's anatomy. The ribbon cable 106 may be a thin-film based cable like those made from polyimide, parylene, or silicone with embedded conductors (e.g., gold, platinum, etc.). The ribbon cable 106 may also include discrete wires, wire bundles, or wire ribbon cables.

The electrode array assembly 108 may comprise an electrode array substrate 300 to support one or more arrays of probe electrodes. These probe electrodes may establish stable and intimate contact with biological tissues compatible with changes within the operating environment. In various embodiments, any number of linear arrays of probes may be combined into a two-dimensional array to produce the electrode array assembly 108. For instance, the electrode array assembly 108 may include a 4×4 array including sixteen contact points that may serve as electrodes. However, the electrode array assembly 108 may be scalable such that, in various embodiments, the electrode array substrate 300 may include arrays and matrices of any dimensions. For example, in one embodiment, the electrode array substrate 300 may include a 2×10 array, while another embodiment may include a 6×7 array. By way of wires or thin-film conductive traces, the flexible ribbon cable 106 may provide electrical connectivity between the electrodes and the electronic circuits and components included in the housing 104.

While in various embodiments, the electrode array substrate 300 may be formed from a rigid material, the depicted electrode array substrate 300 is formed from a thin-film flexible material that permits the electrode array substrate 300 to deform. The deformation of the electrode array substrate 300 permits the substrate 300 to conform to the exterior surface of the portion of the body to be monitored and/or stimulated by the electrodes of the electrode array substrate 300. Additionally, the deformation of the electrode array substrate 300 may enable the individual contact points serving as electrodes to move towards each other or away from each other as the underlying tissue expands and contracts, flexes, or relaxes. Like the ribbon cable 106, the electrode array substrate 300 may include a thin-film based substrate made from polyimide, parylene, or silicone with embedded conductors (e.g., gold, platinum, etc.) that may electrically couple to the contact points serving as electrodes.

Electromechanical features of the structure of the electrode array assembly 108 in connection with cardiac application of the electrode array system 100 will now be described. In various embodiments, the electrode array substrate 300 of the electrode array assembly 108 may be soft and flexible to allow the electrode array substrate 300 to be compliant and match the curvilinear contours of biological tissues of a patient's heart. In addition to being flexible, the electrode array substrate 300 may be configured to include elastic spring-like properties such that the electrode array substrate 300 may deform in various ways to stretch, twist, buckle, and/or bend to withstand the tensile loads produced within the operating environment. That is, the electrode array substrate 300 may be provided with appropriate stiffness to enable reliable electrical contact and mechanical coupling with the biological tissues without exerting mechanically induced discomfort to the patient. This allows the electrode array substrate 300 to maintain robust conformal contact under natural deformations associated with anatomical movements such as muscle contractions. In case the electrode array substrate 300 peels off the biological tissue, it may be configured to fold and stick to itself to avoid causing trauma to the tissue.

In various embodiments, the electrode array substrate 300 may use surface tension to maintain continuous contact with the biological tissues. A fluid such as a hydrogel may be used to move the electrode array substrate 300 over the biological tissue. In addition, the flexible ribbon cable 106 may enable constant electronic integration of the electrodes with the electronic circuits and components within the housing 104 for data collection and communication. In this way, the electrode array substrate 300 may be provided with structural reinforcements to yield a wide range of desired mechanical responses to changes within the operating environment while enabling predictable and reliable functionality of stimulating and/or sensing the biological tissues.

Figure 4:
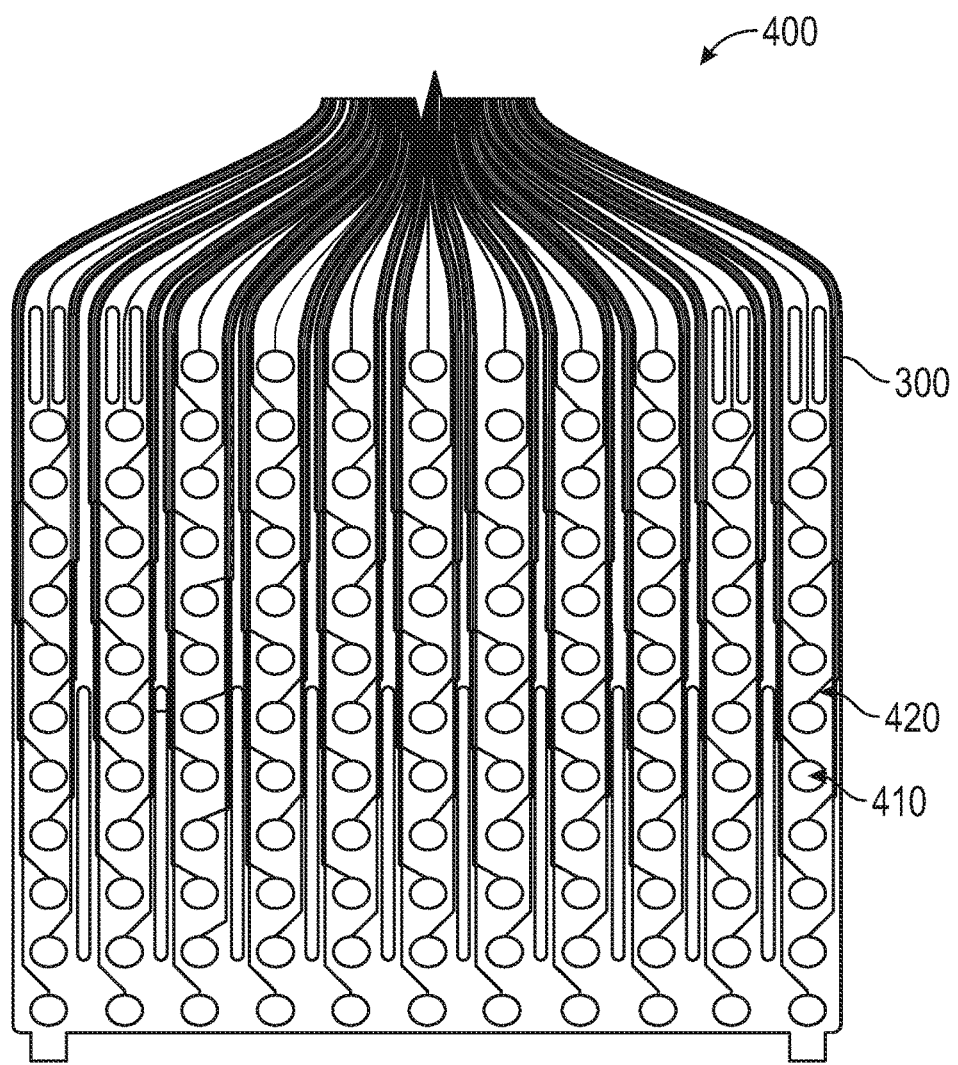
FIG. 4 shows an exemplary configuration 400 of an electrode array assembly according to an embodiment of the present disclosure.

FIG. 4 shows an exemplary configuration 400 of the electrode array assembly 108 according to an embodiment of the present disclosure. In this configuration 400, the electrode array substrate 300 may be a flexible substrate or printed circuit board including electrical contacts 410 with respective traces 420. As shown in FIG. 4, the electrical contacts 410 may be arranged in a row and column configuration, with the respective traces originating at the flexible ribbon cable 106 and running down the columns to terminate at their dedicated electrical contacts 410. In various embodiments, the electrical contacts 410 may be electrodes. In other embodiments, the electrical contacts 410 may be used to connect additional flex ribbon cables and/or arrays.

In some embodiments, each of the electrical contacts 410 may include a respective probe that includes one or more external electrodes affixed to the electrical contact or a corresponding bond pad via an electrical connection. In other embodiments, each of the electrical contacts 410 may be implemented as, as part of, or using a corresponding bond pad of the electrode array substrate 300.

Each trace 420 may be a conductive lead (e.g., gold, titanium, platinum, a metal alloy, or any combination of these materials) and may provide electrical connectivity between the respective electrical contact 410 and the flexible ribbon cable 106. As discussed previously, the flexible ribbon cable 106 provides electrical connectivity between the electronic circuits and components in the housing 104 and the electrodes included in the electrode array. In this way, electrical connectivity is provided between the electrodes and the electronic circuits and components in the housing 104 for data collection and communication.

FIG. 5 shows the exemplary configuration 400 of the electrode array assembly 108 in contact with exterior biological tissue 510 of a patient's heart, according to an embodiment of the present disclosure. In various embodiments, the electrode array substrate 300 flexibly contacts and matches the curvilinear contour of the exterior biological tissue 510 of the patient's heart, allowing for tissue stimulation and sensing as part of the data collection and communication.

FIG. 6 shows another exemplary configuration 600 of the electrode array assembly 108 according to an embodiment of the present disclosure. In this configuration 600, the electrode array substrate 300 may be a flexible substrate or printed circuit board including electrical contact 610 with respective traces 620. The electrode array substrate 300 may also include one or more protruding portion 630 with a hole that serves as an anchor point for suture during the cardiac medical procedure. As shown in FIG. 6, the electrical contacts 610 may be arranged in rows with the electrical contacts 610 being disposed on either side of the traces 620. In various embodiments, the electrical contact 610 may be electrodes.

In some embodiments, each of the electrical contacts 610 may include a respective probe that includes one or more external electrodes affixed to the electrical contact or a corresponding bond pad via an electrical connection. In other embodiments, each of the electrical contacts 610 may be implemented as, as part of, or using a corresponding bond pad of the electrode array substrate 300.

Each trace 620 may be a conductive lead (e.g., gold and/or platinum) and may provide electrical connectivity between the respective electrical contact 610 and the flexible ribbon cable 106. As discussed previously, the flexible ribbon cable 106 provides electrical connectivity between the electronic circuits and components in the housing 104 and the electrodes included in the electrode array. In this way, electrical connectivity is provided between the electrodes and the electronic circuits and components in the housing 104 for data collection and communication.

FIG. 7 shows the exemplary configuration 600 of the electrode array assembly 108 in contact with exterior biological tissue 710 of a patient's heart, according to an embodiment of the present disclosure. In various embodiments, the electrode array substrate 300 flexibly contacts and matches the curvilinear contour of the exterior biological tissue 710 of the patient's heart, allowing for tissue stimulation and sensing as part of the data collection and communication.

FIG. 8 shows another exemplary configuration 800 of the electrode array assembly 108 according to an embodiment of the present disclosure. In this configuration 800, the electrode array substrate 300 may be a flexible substrate or printed circuit board including electrical contacts 810 with respective traces 820. As shown in FIG. 8, the electrical contacts 810 may be arranged in rows with the electrical contacts 810 being disposed in a row and column formation with the respective traces 820 originating from an integrated flexible ribbon cable 106 disposed in a central portion of the electrode array substrate 300. In various embodiments, the thin-film flexible ribbon cable 106 may be folded at bends using a method that results in a single linear cable, thereby allowing long flexible ribbon (e.g., 20 cm) cables 106 to be made on substantially small wafers (e.g., 10 cm in diameter). At the proximal end of the flexible ribbon cable 106, the wires or the thin-film conductive traces terminate in electrode contacts 830. In various embodiments, the electrical contacts 810 may be electrodes.

In some embodiments, each of the electrical contacts 810 may include a respective probe that includes one or more external electrodes affixed to the electrical contact or a corresponding bond pad via an electrical connection. In other embodiments, each of the electrical contacts 810 may be implemented as, as part of, or using a corresponding bond pad of the electrode array substrate 300.

Each trace 820 may be a conductive lead (e.g., gold and/or platinum) and may provide electrical connectivity between the respective electrical contact 810 and the integrated flexible ribbon cable 106. As discussed previously, the flexible ribbon cable 106 provides electrical connectivity between the electronic circuits and components in the housing 104 and the electrodes included in the electrode array. In this way, electrical connectivity is provided between the electrodes and the electronic circuits and components in the housing 104 for data collection and communication.

FIG. 9 shows another exemplary configuration 900 of the electrode array assembly 108 according to an embodiment of the present disclosure. In this configuration 900, the electrode array substrate 300 may be a flexible substrate including electrical contacts 910 with respective traces 920. The electrode array substrate 300 may also include one or more protruding portion 930 with a hole that serves as an anchor point for suture during the cardiac medical procedure. As shown in FIG. 9, the electrode array substrate 300 may be provided in a wing-like structure including a plurality of wings. The electrical contacts 910 may be arranged on the plurality of wings with the electrical contacts 910 being disposed on either side of the traces 920. Alternatively, the thin-film traces in the flexible ribbon cable 106 may be routed under the electrical contacts 910. Additionally, the electrode array substrate 300 may include removable tethers 940 connecting adjacent rows of electrical contacts 910 with each other. In various embodiments, a given row of electrical contacts 910 may be connected to an adjacent row of electrical contacts 910 via two or more removable tethers 940. The removable tethers 940 allow for adjacent rows of electrical contacts 910 to be separated from each other to enable improved handling and maneuverability of the electrode array substrate 300 along the curvilinear exterior tissue of a patient's heart.

In various embodiments, the electrical contacts 910 may be electrodes. In some embodiments, each of the electrical contacts 910 may include a respective probe that includes one or more external electrodes affixed to the electrical contact or a corresponding bond pad via an electrical connection. In other embodiments, each of the electrical contacts 910 may be implemented as, as part of, or using a corresponding bond pad of the electrode array substrate 300.

Each trace 920 may be a conductive lead (e.g., gold and/or platinum) and may provide electrical connectivity between the respective electrical contacts 910 and the flexible ribbon cable 106. As discussed previously, the flexible ribbon cable 106 provides electrical connectivity between the electronic circuits and components in the housing 104 and the electrodes included in the electrode array. In this way, electrical connectivity is provided between the electrodes and the electronic circuits and components in the housing 104 for data collection and communication.

FIG. 10 shows the exemplary configuration 900 of the electrode array assembly 108 in contact with exterior biological tissue 1010 of a patient's heart, according to an embodiment of the present disclosure. In various embodiments, the electrode array substrate 300 flexibly contacts and matches the curvilinear contour of the exterior biological tissue 1010 of the patient's heart, allowing for tissue stimulation and sensing as part of the data collection and communication.

FIG. 11A shows exemplary electrical connections associated with the configuration 900 of the electrode array assembly 108 according to an embodiment of the present disclosure. As discussed above, each electrical contact 910, or any electrode electrically affixed to the electrical contact 910 or a corresponding bond pad, is electrically connected to a distal end of the flexible ribbon cable 106 via a respective trace 920. As shown in FIG. 11A, a proximal end of the flexible ribbon cable 106 may be connected to a printed circuit board 1110 including pins or electrode contacts 1120 that enable electrical connectivity between the flexible ribbon cable 106 and the electronic circuits and components within the housing 104.

FIG. 11B shows an enlarged view of the printed circuit board 1110 from FIG. 11A according to an embodiment of the present disclosure. In various embodiments, the printed circuit board 1110 may include a dedicated pin or electrode contact 1120 that is electrically connected to each electrical contact 910 via the flexible ribbon cable 106.

FIG. 12A shows another exemplary configuration 1200 of the electrode array assembly 108 according to an embodiment of the present disclosure. In this configuration 1200, the electrode array substrate 300 may be a flexible substrate or printed circuit board including electrical contacts 1210 with respective traces 1220. As shown in FIG. 12A, the electrical contacts 1210 may be arranged in one or more paddle formations with the electrical contacts 1210 being disposed on either side of the traces 1220, which may be included in the flexible ribbon cable 106 disposed along a central portion of the paddle formations. The flexible ribbon cable 106 connects one or more paddle formations with each other.

In various embodiments, the electrical contacts 1210 may be electrodes. In various embodiments, the electrical contacts 1210 may be electrodes. In some embodiments, each of the electrical contacts 1210 may include a respective probe that includes one or more external electrodes affixed to the electrical contact or a corresponding bond pad via an electrical connection. In other embodiments, each of the electrical contacts 1210 may be implemented as, as part of, or using a corresponding bond pad of the electrode array substrate 300.

Each trace 1220 may be a conductive lead (e.g., gold and/or platinum) and may provide electrical connectivity between the respective electrical contact 1210 and the flexible ribbon cable 106. As discussed previously, the flexible ribbon cable 106 provides electrical connectivity between the electronic circuits and components in the housing 104 and the electrodes included in the electrode array. In this way, electrical connectivity is provided between the electrodes and the electronic circuits and components in the housing 104 for data collection and communication.

FIG. 12B shows a proximal end of the flexible ribbon cable 106, according to an embodiment of the present disclosure. At the proximal end, the flexible ribbon cable 106 may be connected to a printed circuit board 1250 including pins or electrode contacts 1260 that enable electrical connectivity between the flexible ribbon cable 106 and the electronic circuits and components within the housing 104. In various embodiments, the printed circuit board 1250 may include a dedicated pin or electrode contact 1260 that is electrically connected to each electrical contact 1210 via the flexible ribbon cable 106.

FIG. 13 shows the exemplary configuration 1200 of the electrode array assembly 108 in contact with exterior biological tissue 1310 of a patient's heart, according to an embodiment of the present disclosure. In various embodiments, the paddle formations 1230, 1240 of the electrode array substrate 300 flexibly contact and match the curvilinear contour of the exterior biological tissue 1310 of the patient's heart, allowing for tissue stimulation and sensing as part of the data collection and communication. Additionally, the portion of the flexible ribbon cable 106 that connects the paddle formations 1230, 1240 with each other may include a bellowed accordion-like portion to allow expansion and contraction of the flexible ribbon cable 106 in the bellowed accordion-like portion to add additional flexibility to the electrode array assembly 108. The expansion and contraction of the flexible ribbon cable 106 in the bellowed accordion-like portion allows a variation in a distance between the paddle formations 1230, 1240.

FIG. 14A shows another exemplary configuration 1400 of the electrode array assembly 108 according to an embodiment of the present disclosure. In this configuration 1400, the electrode array substrate 300 may be a flexible substrate or printed circuit board including electrical contacts 1410 with respective traces 1420. As shown in FIG. 14A, the electrical contacts 1410 may be arranged in row formations, with the traces 1420 being arranged in a planar spring or coil-like structure to add springiness and flexibility to the electrode array assembly 108. In various embodiments, the electrical contacts 1410 may be connected to the flexible ribbon cable 106 by the traces 1420 such that the electrical contacts 1410 float in the assembly. Robustness may be added to the structure of the coil through polyimide annealing to enable maintenance of a shape of the spring or coil-like structure. In various embodiments, shape memory polymers or shape memory alloys such as nitinol may be used to construct the spring or coil-like structure.

In various embodiments, the electrical contacts 1410 may be electrodes. In various embodiments, the electrical contacts 1410 may be electrodes. In some embodiments, each of the electrical contacts 1410 may include a respective probe that includes one or more external electrodes affixed to the electrical contact or a corresponding bond pad via an electrical connection. In other embodiments, each of the electrical contacts 1410 may be implemented as, as part of, or using a corresponding bond pad of the electrode array substrate 300.

Each trace 1420 may be a conductive lead (e.g., gold and/or platinum) and may provide electrical connectivity between the respective electrical contact 1410 and the flexible ribbon cable 106. As discussed previously, the flexible ribbon cable 106 provides electrical connectivity between the electronic circuits and components in the housing 104 and the electrodes included in the electrode array. In this way, electrical connectivity is provided between the electrodes and the electronic circuits and components in the housing 104 for data collection and communication.

FIG. 14B shows a proximal end of the flexible ribbon cable 106, according to an embodiment of the present disclosure. At the proximal end, the flexible ribbon cable 106 may be connected to a printed circuit board 1450 including pins or electrode contacts 1460 that enable electrical connectivity between the flexible ribbon cable 106 and the electronic circuits and components within the housing 104. In various embodiments, the printed circuit board 1450 may include a dedicated pin or electrode contact 1460 that is electrically connected to each electrical contact 1410 via the flexible ribbon cable 106.

FIG. 15 shows another view of the exemplary electrode array assembly 108 of configuration 1400.

FIG. 16 shows the exemplary configuration 1500 of the electrode array assembly 108 in contact with exterior biological tissue 1610 of a patient's heart, according to an embodiment of the present disclosure. In various embodiments, the electrode array substrate 300 may be attached to a flexible mesh carrier 1630 to flexibly contact and match the curvilinear contour of the exterior biological tissue 1610 of the patient's heart, allowing for tissue stimulation and sensing as part of the data collection and communication. FIG. 17 shows another view of the exemplary configuration 1500 with the electrode array substrate 300 attached to the flexible mesh carrier 1630 in contact with exterior biological tissue 1610 of a patient's heart.

FIG. 18 shows another exemplary configuration 1800 of the electrode array assembly 108 according to an embodiment of the present disclosure. In this configuration 1800, the electrode array substrate 300 may be a flexible substrate or printed circuit board including electrical contacts 1810 with respective traces 1820. As shown in FIG. 18, the electrical contacts 1810 may be arranged in a row and column "meso" formation with dedicated traces 1820 electrically connecting each electrical contact 1810 to the flexible ribbon cable 106. In various embodiments, the formation includes traces 1820 originating at the flexible ribbon cable 106 and terminating at the dedicated electrical contacts 1810. The dedicated traces 1820 may include a spring-like structure to add flexibility to the electrode array substrate 300.

In various embodiments, the electrical contacts 1810 may be electrodes. In various embodiments, the electrical contacts 1810 may be electrodes. In some embodiments, each of the electrical contacts 1810 may include a respective probe that includes one or more external electrodes affixed to the electrical contact or a corresponding bond pad via an electrical connection. In other embodiments, each of the electrical contacts 1810 may be implemented as, as part of, or using a corresponding bond pad of the electrode array substrate 300.

Each trace 1820 may be a conductive lead (e.g., gold and/or platinum) and may provide electrical connectivity between the respective electrical contact 1810 and the flexible ribbon cable 106. As discussed previously, the flexible ribbon cable 106 provides electrical connectivity between the electronic circuits and components in the housing 104 and the electrodes included in the electrode array. In this way, electrical connectivity is provided between the electrodes and the electronic circuits and components in the housing 104 for data collection and communication.

FIG. 19A shows another exemplary configuration 1900 of the electrode array assembly 108 according to an embodiment of the present disclosure. In this configuration 1900, the electrode array substrate 300 may be a flexible substrate or printed circuit board including electrical contacts 1910 with respective traces 1920. As shown in FIG. 19A, the electrical contacts 1910 may be arranged in another row and column "meso" formation with dedicated traces 1920 electrically connecting each electrical contact 1910 to the flexible ribbon cable 106. In various embodiments, the formation includes traces 1920 originating at the flexible ribbon cable 106 and terminating at the dedicated electrical contacts 1910. The dedicated traces 1920 may include a spring-like structure to add flexibility to the electrode array substrate 300.

In various embodiments, the electrical contacts 1910 may be electrodes. In various embodiments, the electrical contacts 1910 may be electrodes. In some embodiments, each of the electrical contacts 1910 may include a respective probe that includes one or more external electrodes affixed to the electrical contact or a corresponding bond pad via an electrical connection. In other embodiments, each of the electrical contacts 1910 may be implemented as, as part of, or using a corresponding bond pad of the electrode array substrate 300.

Each trace 1920 may be a conductive lead (e.g., gold and/or platinum) and may provide electrical connectivity between the respective electrical contact 1910 and the flexible ribbon cable 106. As discussed previously, the flexible ribbon cable 106 provides electrical connectivity between the electronic circuits and components in the housing 104 and the electrodes included in the electrode array. In this way, electrical connectivity is provided between the electrodes and the electronic circuits and components in the housing 104 for data collection and communication.

FIG. 19B shows a proximal end of the flexible ribbon cable 106 according to an embodiment of the present disclosure. At the proximal end, the flexible ribbon cable 106 may be connected to a printed circuit board 1950 including pins or electrode contacts 1960 that enable electrical connectivity between the flexible ribbon cable 106 and the electronic circuits and components within the housing 104. In various embodiments, the printed circuit board 1950 may include a dedicated pin or electrode contact 1960 that is electrically connected to each electrical contact 1910 via the flexible ribbon cable 106.

FIG. 20 shows another view of the exemplary electrode array assembly 108 of configuration 1900.

FIG. 21 shows another exemplary configuration 2100 of the electrode array assembly 108 according to an embodiment of the present disclosure. In this configuration 2100, the electrode array substrate 300 may be a flexible substrate or printed circuit board including electrical contacts 2110 with respective traces 2120. As shown in FIG. 21, the electrical contacts 2110 may be arranged in another row and column "meso" formation with dedicated traces 2120 electrically connecting each electrical contact 2110 to the flexible ribbon cable 106. In various embodiments, the formation includes electrical contacts 2110 included in each column being electrically connected to the flexible ribbon cable 106 through traces 2120 originating at the flexible ribbon cable 106 and running down the columns to terminate at their dedicated electrical contacts 2110. The flexible electrode array substrate 300 may be connected to an integrate frame 2130, which may help support the flexible substrate during manufacturing. Thin connection points 2140, which connection the flexible substrate to the integrate frame 2130, may be cut to release the flexible substrate from the frame prior to use in the operating environment.

In various embodiments, the electrical contacts 2110 may be electrodes. In various embodiments, the electrical contacts 2110 may be electrodes. In some embodiments, each of the electrical contacts 2110 may include a respective probe that includes one or more external electrodes affixed to the electrical contact or a corresponding bond pad via an electrical connection. In other embodiments, each of the electrical contacts 2110 may be implemented as, as part of, or using a corresponding bond pad of the electrode array substrate 300.

Each trace 2120 may be a conductive lead (e.g., gold and/or platinum) and may provide electrical connectivity between the respective electrical contact 2110 and the flexible ribbon cable 106. As discussed previously, the flexible ribbon cable 106 provides electrical connectivity between the electronic circuits and components in the housing 104 and the electrodes included in the electrode array. In this way, electrical connectivity is provided between the electrodes and the electronic circuits and components in the housing 104 for data collection and communication.

FIG. 22 shows the exemplary configuration 2100 of the electrode array assembly 108, according to an embodiment of the present disclosure. In various embodiments, the electrode array substrate 300 may be attached to a flexible plastic carrier 2230 to flexibly contact and match the curvilinear contour of the exterior biological tissue of the patient's heart, allowing for tissue stimulation and sensing as part of the data collection and communication.

FIG. 23 shows another view of the exemplary configuration 2100 with the electrode array substrate 300 attached to a flexible woven mesh carrier 2230 to flexibly contact and match the curvilinear contour of the exterior biological tissue of the patient's heart. The mesh carrier 2230 may be formed of non-conducting bio-compatible material. FIG. 24 shows another view of the exemplary configuration 2100 with the electrode array substrate 300 attached to the flexible woven mesh carrier 2230. FIG. 25 shows another view of the exemplary configuration 2100 with the electrode array substrate 300 attached to a flexible and stretchable silicone carrier 2530 to flexibly contact and match the curvilinear contour of the exterior biological tissue of the patient's heart. FIG. 26 shows the exemplary configuration 2100 of the electrode array assembly 108 in contact with exterior biological tissue 2610 of a patient's heart, according to an embodiment of the present disclosure. In various embodiments, the electrode array substrate 300 flexibly contacts and matches the curvilinear contour of the exterior biological tissue 2610 of the patient's heart, allowing for tissue stimulation and sensing as part of the data collection and communication.

FIG. 27 shows another exemplary configuration 2700 of the electrode array assembly 108 according to an embodiment of the present disclosure. In this configuration 2700, the electrode array substrate 300 may be a flexible substrate or printed circuit board including electrical contacts 2710 with respective traces 2720. As shown in FIG. 27, the electrical contacts 2710 may be arranged in a row and column "meso" formation with dedicated traces 2720 electrically connecting each electrical contact 2710 to the flexible ribbon cable 106. In various embodiments, the formation includes electrical contacts 2710 included in each column being electrically connected to the flexible ribbon cable 106 through traces 2720 originating at the flexible ribbon cable 106 and running down the columns to terminate at their dedicated electrical contacts 2710.

In various embodiments, the electrode array substrate 300 may be provided a bank of springs 2730 at an end of the electrode array substrate 300 proximal to the flexible ribbon cable 106. The springs included in the bank of springs 2730 flex to isolate the flexible ribbon cable 106 from tensile forces in the operating environment. FIG. 28 shows the exemplary configuration 2700 of the electrode array assembly 108 in contact with exterior biological tissue 2810 of a patient's heart, according to an embodiment of the present disclosure. In various embodiments, the electrode array substrate 300 flexibly contacts and matches the curvilinear contour of the exterior biological tissue 2810 of the patient's heart, allowing for tissue stimulation and sensing as part of the data collection and communication. FIG. 29 shows another view of the exemplary configuration 2700 of the electrode array assembly 108 in contact with exterior biological tissue 2810 of a patient's heart, according to an embodiment of the present disclosure.

Referring now to FIG. 30, there is shown an inserter 3000 for holding a flexible array 3050 similar to those described above. The inserter 3000 includes four tubes 3010, 3012, 1014 and 3016 positioned at the corners of the assembly. Suction is applied to the tubes such that the securely hold the thin film. Suction is applied through tube 3020 to the assembly and the tubes are in fluid communication with the tube 3020. The tubes are formed of relatively soft material, such as silicon, such that they flex rather than poke tissue. This can be important as the inserter and thin film are moved toward a beating heart. As will be appreciated, thin films can be delicate/flimsy and difficult to handle and may be damaged during the insertion process if handled improperly. To place the thin film array, suction is first applied to engage the thin film array to the inserter, then the thin film is positioned on the tissue (such as heart), such is removed and the thin film array clings to the wet tissue. The inserter can then be disengaged from the thin film array. If the array need to be repositioned, suction can again be applied to the inserter to have the film sucked toward the tubes.

Although some exemplary embodiments show implementation with one electrode array substrate 300 electrically connected to electronic components and circuits, the present disclosure also contemplates a modular system capable of supporting multiple electrode array substrates 300. Additionally, the multiple electrode array substrates 300 may be of the same or different configuration.

In one application, the electrode array is positioned on the tissue of interest, such as the heart, initial readings of tissue conductivity, resistance, inductance and/or capacitance are obtained for one or more electrodes. Preferably, this information would be obtained for all electrodes. The information is stored as an initial data set. Periodically, the same types of tests are conducted to determine changes from the initial data set. This information can be used to determine whether migration of the array has occurred. Such information can assist with data integrity and advise the user that certain processing steps may need to be taken to correlate the data to take into account small migrations. Also, the user can repeat the process until a valid set of data is obtained from a set location for a set amount of time.

FIG. 31 shows another exemplary configuration 3100 of the electrode array assembly 108 according to an embodiment of the present disclosure. In this configuration 3100, the electrode array substrate 300 may be a flexible substrate or printed circuit board including electrical contacts 3110 affixed to bond pads 3112 and respective traces 3120 electrically connected to electrical contacts 3110.

The bond pads 3112 may be arranged in a row and column "meso" formation with dedicated traces 3120 electrically connecting each electrical contact 3110 affixed to each bond pad 3112 to the flexible ribbon cable 106. In various embodiments, the formation includes electrical contacts 3110 included in each column being electrically connected to the flexible ribbon cable 106 through traces 3120 originating at the flexible ribbon cable 106 and running down the columns to terminate at their dedicated electrical contacts 3110.

In various embodiments, the electrical contacts 3110 may be electrodes. In some embodiments, each of the electrical contacts 3110 may include a respective probe that includes one or more external electrodes affixed to the electrical contact or a corresponding bond pad via an electrical connection. In other embodiments, each of the electrical contacts 3110 may be implemented as, as part of, or using a corresponding bond pad of the electrode array substrate 300.

In other embodiments, only a portion of the bond pads 3112 may have electrical contacts 3110 affixed to them. Accordingly, the electrical contacts 3110 may have a symmetrical or non-symmetrical configuration, depending on the implementation.

Each trace 3120 may be a conductive lead (e.g., gold and/or platinum) and may provide electrical connectivity between the respective electrical contact 3110 and the flexible ribbon cable 106. As discussed previously, the flexible ribbon cable 106 provides electrical connectivity between the electronic circuits and components in the housing 104 and the electrodes included in the electrode array. In this way, electrical connectivity is provided between the electrodes and the electronic circuits and components in the housing 104 for data collection and communication.

In one or more embodiments, at least a portion of the electrical contacts 3110 may take the form of electrode pairs affixed to bond pads 3112. For example, the electrode pair 3122 is affixed to the bond pad 3124. The electrode pair 3122 includes an electrode 3126 and an electrode 3128. In one or more embodiments, the electrode pair 3122 is a concentric electrode pair in which the electrode 3126 is the center electrode and the electrode 3128 is a ring electrode disposed around the center electrode. In other embodiments, the electrode 3126 and the electrode 3128 may have different shapes or configurations that form a closely-spaced electrode pair 3122. For example, in some cases, the electrode 3126 and the electrode 3128 may be probes positioned adjacent to each other over bond pad 3124. In still other cases, an electrode pair may be affixed to a particular electrical contact 3110 that is affixed to bond pad 3124.

Additionally, having electrode pairs may allow simultaneous stimulation and sensing modes from a substantially same position or location. For example, the electrode 3126 may be used for stimulation, while the electrode 3128 may be used for sensing, or vice versa. In some embodiments, having at least a portion of the electrical contact 3110 with electrode pairs, similar to the electrode pair 3122, affixed to the electrical contacts 3110 may help reduce noise. For example, one of the electrodes in the electrode pair 3122 may be used as a reference electrode so that "noise" in the signal received from the other electrode may be more precisely filtered out.

The flexible electrode array substrate 300 may be connected to a frame 3130, which may help support the flexible substrate during manufacturing. Thin connection points 3140, which connect the flexible electrode array substrate 300 to the frame 3130, may be cut to release the flexible electrode array substrate 300 from the frame prior to use in the operating environment.

As depicted in FIG. 31, the electrode array substrate 300 may include connecting portions 3142 that connect the various electrical contacts 3110. In one or more embodiments, each of connecting portions 3142 connects a pair of electrical contacts in a same row or a pair of electrical contacts in a same column. In other embodiments, the electrical contacts 3110 may be arranged in a staggered formation such that the electrical contacts on one row are aligned with the connecting portions on each adjacent row. Of course, in still other illustrative embodiments, the electrical contacts 3110 may be arranged in a circular pattern or some other type of geometric pattern. Connecting portions 3142 are shaped and arranged to provide an additional degree of flexibility between the electrical contacts 3110 and to allow stretching between the electrical contacts 3110.

FIG. 32 is a flowchart of a process for assembling a flexible electrode array system, according to an embodiment of the present disclosure. Process 3200 may be used to assemble, for example, flexible electrode array assembly 108 having electrode array substrate 300 with any of the configurations of the various embodiments described above.

Process 3200 begins by providing a plurality of electrical contacts disposed on a thin-film substrate, the plurality of electrical contacts providing electrical contact points (step 3202). In some embodiments, an electrical contact may take the form of an electrode. In one or more embodiments, the electrical contact may take the form of a single electrode or an electrode pair. In some cases, the electrode pair may be a pair of concentrically aligned electrodes. In some embodiments, an electrical contact may be affixed to a bond pad. In other embodiments, an electrical contact may be considered a bond pad or a part of a bond pad.

Next, a plurality of traces is electrically connected to the plurality of electrical contacts (step 3204). At step 3204, an electrical contact of the plurality of electrical contacts has a corresponding dedicated trace of the plurality of traces that provides electrical connectivity to the electrical contact. The thin-film substrate is configured to flex to maintain continuous contact with contours of patient anatomy. The thin-film substrate may maintain continuous contact with the contours of the patient anatomy using, for example, surface adhesion with respect to the patient anatomy. In some embodiments, the thin-film substrate may be disposed on a flexible woven mesh carrier.

In one or more embodiments, the plurality of traces includes flexible spring-like portions to add flexibility to the thin-film substrate. For example, at step 3204, electrically connecting the plurality of traces to the plurality of electrical contacts includes electrically connecting the flexible spring-like portions to the plurality of electrical contacts to provide a degree of flexibility at the locations of the plurality of electrical contacts. Optionally, the plurality of traces may be electrically connected to a housing via a flexible ribbon cable (step 3206).

Thus, the various example embodiments described below provide a flexible electrode array system that includes a thin-film substrate and a plurality of electrode contacts disposed on the thin-film substrate. A plurality of traces is electrically connected to the plurality of electrode contacts. An electrical contact of the plurality of electrode contacts having at least one dedicated trace of the plurality of traces configured to provide electrical connectivity to the electrode contact. The thin-film substrate is configured to flex to maintain continuous contact with contours of patient anatomy. In some embodiments, the plurality of traces may include flexible spring-like portions to add flexibility to the thin-film substrate.

In one or more embodiments, the electrode contacts in the various example embodiments described above may be arranged in an arbitrary layout or a predetermined formation. For example, the electrode contacts may be disposed in at least one of a row and column formation, a symmetrical formation, a non-symmetrical formation, an irregular formation, rectilinear formation, a circular formation, a spiral formation, a triangular formation, a paddle formation, a multi-paddle formation, a hexagonal formation, an L-shaped formation, or in some other type of formation. In some cases, this formation may match a shape or structural configuration of the thin-film substrate. In other examples, this formation may be different from the shape or structural configuration of the thin-film substrate. In yet other embodiments, the electrode contacts may be arranged in a group in order to record and/or stimulate the adjacent tissue region in a selected or predetermined manner. For example, this layout for the electrical contacts may be designed for the detection of particular bioelectrical features, such as waves/features of tissue activation and/or inhibition.

In some embodiments, an electrode contact may have multiple traces that connect to one or multiple electrical contacts or one or more bond pads in order to provide redundancy and fault-tolerance. For example, if one trace does not work as desired, the companion traces would be able to make the necessary electrical connections.

In one or more embodiments, an electrode array may include a subset of electrode contacts for providing one type of operation and another subset of electrode contacts for providing another type of operation or combination of operations. For example, a first subset of electrode contacts may be dedicated to electrical stimulation, while a second subset of electrode contacts may be dedicated to recording. In still other cases, a subset of electrode contacts may be dedicated to both stimulation and recording (e.g., electrode pairs).

Electrode contacts may vary in size in order to provide certain electrical and electrode/tissue characteristics or information. For example, a larger electrical contact may be designed to provide an electrical reference. Thus, a single electrode array system may include electrode contacts of various sizes.

In some embodiments, the thin-film substrate or the backing to the thin-film substrate may be non-uniform in order to provide mechanical and/or electromechanical characteristics or information. For example, flexible spring-like portions may be electrically connected to the electrical contacts or a portion of the electrical contacts in a non-uniform manner to provide strain relief in one direction over another direction.

Thus, the electrode array system may be configured in a variety of ways. While certain exemplary embodiments of the disclosure have been described and shown in the accompanying drawings, it is to be understood that such embodiments are merely illustrative of and not restrictive on the broad disclosure, and that the embodiments of the disclosure not be limited to the specific constructions and arrangements shown and described, since various other modifications may occur to those ordinarily skilled in the art.

What is claimed is:

1. A medical electrode array system for application to a beating heart, comprising:
    a soft and flexible thin-film substrate compliant to match curvilinear contours of biological tissues of the beating heart;
    a plurality of electrode contacts disposed on the thin-film substrate, the plurality of electrode contacts configured to provide electrical contact points; and
    a plurality of traces electrically connected to the plurality of electrode contacts, at least a subset of the plurality of electrode contacts each have a dedicated trace of the plurality of traces that provide electrical connectivity to the respective electrode contact,
    wherein the plurality of traces includes flexible spring-like structures to add flexibility to the thin-film substrate;
    wherein the flexible spring-like structures are configured to stretch and bend to withstand tensile loads produced by muscle contractions within the beating heart;
    wherein the dedicated trace of the plurality of traces includes a spring-like structure on a first side of the electrode contact; and
    wherein the thin-film substrate comprises a plurality of flexible connecting elements;
    wherein a first flexible connecting element of the plurality of flexible connecting elements is located on a second side of the first electrode contact and couples the electrode contact with an adjacent electrode contact without a trace, wherein the second side is perpendicular to the first side; and
    wherein a second flexible connecting element of the plurality of flexible connecting elements is located on a third side of the electrode contact and supports at least one trace of the plurality of traces.

2. The medical electrode array system of claim 1, wherein the thin-film substrate is configured to use only surface tension to maintain continuous contact with respect to the beating heart.

3. The medical electrode array system of claim 1, wherein the plurality of traces may be electrically connected to a flexible cable to enable electrical connectivity between control circuitry and the plurality of electrode contacts.

4. The medical electrode array system of claim 1, wherein:
    the plurality of electrode contacts are disposed on the thin-film substrate in at least one of a row and column formation, a symmetrical formation, a non-symmetrical formation, or an irregular formation, and the plurality of traces are formed vertically along columns of the row and column formation such that each dedicated trace terminates at one or more predetermined electrode contacts.

5. The medical electrode array system of claim 1, wherein the plurality of electrode contacts are disposed on the thin-film substrate in a row formation such that electrode contacts lie on either side of their dedicated plurality of traces.

6. The medical electrode array system of claim 1, wherein the thin-film substrate is disposed on a flexible non-conducting carrier.

7. The medical electrode array system of claim 1, wherein the thin-film substrate is disposed on a bio-compatible woven mesh carrier.

8. The medical electrode array system of claim 1, wherein the thin-film substrate includes a bank of springs in a portion of the thin-film substrate proximal to a flexible cable to isolate the flexible cable from surrounding tensile forces.

9. The medical electrode array system of claim 1, wherein the plurality of electrode contacts on the thin-film substrate are electrically connected to a plurality of flexible cables.

10. The medical electrode array system of claim 1, wherein the electrical contact points of the plurality of electrode contacts are configured to electrically connect to electrodes.

11. The medical electrode array system of claim 1, wherein the plurality of electrode contacts are disposed on the thin-film substrate in a row and column formation; and wherein the dedicated trace follows a subset of the plurality of electrode contacts along a column.

12. The medical electrode array system of claim 1, wherein a second spring-like structure of is at a first side of a second electrode contact.

13. The medical electrode array system of claim 1, further comprises:
a frame; and
a plurality of connection points, wherein the plurality of connection points connect the thin-film substrate to the frame.

14. A medical electrode array system for application to a beating heart, comprising:
a soft and flexible thin-film substrate compliant to match curvilinear contours of biological tissues of the beating heart;
a plurality of electrode contacts disposed on the thin-film substrate, the plurality of electrode contacts arranged in a row and column formation;
a plurality of traces electrically connected to the plurality of electrode contacts,
at least a subset of the plurality of electrode contacts each have a dedicated trace of the plurality of traces that provide electrical connectivity to the respective electrode contact,
wherein a trace of the plurality of traces runs down a column of the row and column formation and ends at a first electrode contact of the plurality of electrode contacts;
wherein the dedicated trace includes a spring-like structure,
the spring-like structure being on a first side of the electrode contact;
wherein the thin-film substrate comprises a plurality of flexible connecting elements;
wherein a first flexible connecting element of the plurality of flexible connecting elements is located on a third side of the electrode contact and couples the electrode contact with an adjacent electrode contact without a trace, wherein the third side is perpendicular to the first side; and
wherein a second flexible connecting element of the plurality of flexible connecting elements is located on a third side of the electrode contact and supports at least one trace of the plurality of traces; and
wherein the spring-like structure is configured to stretch and bend to withstand tensile loads produced by muscle contractions within the beating heart.

15. The medical electrode array system of claim 14, wherein the thin-film substrate has a first end and a second end and further comprising:
a bank of springs at the first end of the thin-film substrate.

16. The medical electrode array system of claim 15, wherein the bank of springs is located between the first end of the thin-film substrate and a flexible ribbon cable and is configured to flex to isolate the flexible ribbon cable from tensile forces.

17. The medical electrode array system of claim 14, further comprising:
a frame integrated with the thin-film substrate, wherein the frame is configured to be cut away prior to use of the medical electrode array system.

18. The medical electrode array system of claim 14, wherein a flexible connecting element of the plurality of flexible connecting elements is located between an adjacent pair of electrode contacts of the plurality of electrode contacts in the column of the row and column formation and wherein the trace follows the flexible connecting element.

19. The medical electrode array system of claim 14, wherein a flexible connecting element of the plurality of flexible connecting elements is located between an adjacent pair of electrode contacts of the plurality of electrode contacts in a row of the row and column formation.

20. The medical electrode array system of claim 14, wherein the plurality of traces have a plurality of spring-like structures that includes the spring-like structure and wherein the plurality of spring-like structures are arranged in the row and column formation.

21. The medical electrode array system of claim 1, wherein the thin-film substrate is configured to provide an appropriate stiffness to enable electrical contact and mechanical coupling with the biological tissues of the beating heart; and wherein the thin-film substrate is further configured to maintain conformal contact with the beating heart under natural deformations associated with anatomical movements of the beating heart.

22. The medical electrode array system of claim 14, wherein the thin-film substrate is configured to provide an appropriate stiffness to enable electrical contact and mechanical coupling with the biological tissues of the beating heart; and wherein the thin-film substrate is further configured to maintain conformal contact with the beating heart under natural deformations associated with anatomical movements of the beating heart.

23. The medical electrode array system of claim 14, wherein the thin-film substrate is configured to use only surface tension to maintain continuous contact with respect to the beating heart.

* * * * *